(12) United States Patent
Michon et al.

(10) Patent No.: US 8,598,337 B2
(45) Date of Patent: Dec. 3, 2013

(54) METHOD FOR PURIFYING POLYSACCHARIDES

(75) Inventors: Francis Michon, Bethesda, MD (US); Catherine Uitz, McLean, VA (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 1779 days.

(21) Appl. No.: 11/622,906

(22) Filed: Jan. 12, 2007

(65) Prior Publication Data

US 2007/0154492 A1    Jul. 5, 2007

Related U.S. Application Data

(60) Provisional application No. 60/758,894, filed on Jan. 13, 2006.

(51) Int. Cl.
*C07H 1/06* (2006.01)

(52) U.S. Cl.
USPC ......... 536/127; 536/123.1; 530/413; 435/101

(58) Field of Classification Search
None
See application file for complete search history.

(56) References Cited

U.S. PATENT DOCUMENTS 4,727,136 A * 2/1988 Jennings et al. ......... 424/197.11
5,097,020 A * 3/1992 Anderson et al. ............. 530/403
5,425,946 A * 6/1995 Tai et al. ................... 424/197.11
6,248,570 B1 * 6/2001 Michon et al. ................. 435/101
6,350,861 B1 * 2/2002 Co et al. .................... 530/388.85
2004/0213804 A1* 10/2004 Michon et al. .............. 424/190.1
2006/0035284 A1 * 2/2006 Granoff et al. ................. 435/7.1

FOREIGN PATENT DOCUMENTS

EP          0238739      *  9/1987
WO          99/32653        7/1999

OTHER PUBLICATIONS

Millipore Pellicon 2 Microfiltration Modules, pp. 1-4, Jul. 26, 2010.*
Jennings et al. Infection and Immunity, vol. 43 No. 1 Jan. 1984, p. 407-412.*
Jennings et al. The Journal of Immunology. vol. 137, 1708-1713, No. 5, Sep. 1, 1986.*
Wessels et al., "Isolation and Characterization of Type IV Group B *Streptococcus* Capsular Polysaccharide", Infection and Immunity, Apr. 1989, vol. 57, No. 4, p. 1089-1094.
PCT International Search Report dated Feb. 4, 2008.

* cited by examiner

*Primary Examiner* — Jennifer Graser
(74) *Attorney, Agent, or Firm* — Marshall, Gerstein & Borun LLP

(57) ABSTRACT

This invention relates to improved methods for purifying polysaccharides from cellular components, such as a cell wall. The method relates to hydrolyzing and separating the polysaccharides, thereby resulting in purified polysaccharides useful for producing antigens, antibodies, and vaccines comprising the polysaccharides alone or conjugated to carrier molecules. This method is simple, rapid, efficient, scalable, and reproducible.

30 Claims, 4 Drawing Sheets

METHOD FOR PURIFYING POLYSACCHARIDES

FIELD OF THE INVENTION

This application claims the benefit of priority to U.S. Provisional Application No. 60/758,894 filed Jan. 13, 2006, and incorporates by reference this entire provisional application in its entirety.

This invention relates to improved methods for purifying polysaccharides. The extracted polysaccharides are useful for producing antigens, antibodies, and vaccines comprising the polysaccharides alone or conjugated to carrier molecules.

BACKGROUND OF THE INVENTION

A great variety of microorganisms cause disease in humans. Bacterial infections are caused by gram-positive and gram-negative bacteria, spirochetes, mycobacteria, rickettsias, chlamydias and mycoplasmas. Yeast and systemic fungal pathogens are also a significant health problem in both the immunocompetent and the immunocompromised host. Cancer is another disease in humans.

Bacterial infections caused by gram-positive bacteria such as *Streptococcus, Staphylococcus, Enterococcus, Bacillus, Corynebacterium, Listeria, Erysipelothrix*, and *Clostridium*, and by gram-negative bacteria such as *Haemophilus, Shigella, Vibrio cholerae, Neisseria* and certain types of *Escherichia coli*, cause serious morbidity throughout the world. This, coupled with the emerging resistance shown by bacteria to currently used antibiotics, indicates the need for the development of bacterial vaccines to avoid these adverse consequences. Many current bacterial vaccine strategies involve the use of polysaccharide-comprising antigens associated with the bacterial cell wall (1, 3, 4, 11, 14, 15, 16, 23, 30, 31, 32, 34, 35, 37, 45, 46, 48).

A common feature for all bacteria, fungi and some protozoa is the presence of polysaccharides in and/or attached to their cell wall. Polysaccharides are an important architectural feature of the cell wall and contribute to the protection of microorganisms from attack by the immune system. Microbes have evolved a variety of different cell wall and cell wall-associated structures to avoid recognition and destruction by both the innate and adaptive arms of the host's immune system. For example, phagocytic cells of the innate immune system have specific cell surface receptors that recognize cell wall and cell wall-associated antigens. The CD14 receptor and Toll-like receptors (TLR) have been demonstrated to recognize peptidoglycan, lipoteichoic acid, and polysaccharide antigens; and in so doing, activate macrophages to phagocytose microorganisms (24, 38, 49). The adaptive arm of the immune system can also respond to these antigens, by generating antibodies that are specific to cell wall polysaccharide structures (29, 41).

Gram-positive and gram-negative bacteria are distinguished by their outer cell surface structure. The gram-positive cell wall is often devoid of lipids and is composed mostly of peptidoglycan, accessory polymers such as teichoic and/or teichuronic acid covalently linked to peptidoglycan, and protein. Peptidoglycan, also known as murein or mucopeptide, is composed of a polysaccharide backbone consisting of alternating repeats of N-acetylglucosamine (NAG) and N-acetylmuramic acid (NAM) with peptide side chains containing D- and L-amino acids. Gram-negative bacteria possess a cell wall composed of an outer membrane and a layer of peptidoglycan embedded between the outer membrane and an inner cytoplasmic membrane. The outer membrane contains lipopolysaccharide (LPS) as well as lipids and proteins. The LPS molecule is composed of a lipid A 'head' that is integrated into the outer membrane and a polysaccharide tail that extends outward from the outer membrane. The polysaccharide tail usually consists of a core oligopolysaccharide and an O-polysaccharide. The O-polysaccharide resembles peptidoglycan in having a basic repeating motif consisting of the alternating composition of N-acetylglucosamine (NAG) and N-acetylmuramic acid (NAM). Also, capsular polysaccharides (CPS) and subcapsular polysaccharides are attached to the outer surface of gram-positive and gram-negative cell walls, and further serve to protect bacterial cells from recognition and engulfment by phagocytes.

Because the polysaccharide-containing components of the bacterial outer surface are specifically recognized by immune receptors, bacteria mutate their outer surface composition. For example, although cell wall polysaccharides are mainly composed of repeating (oligo)polysaccharide units, bacterial sub-strains vary this basic structure by having different modifications and/or ordering of the polysaccharide units. For instance, Group B *Streptococci* have a group antigen common to all serotypes (i.e., group polysaccharides (GPS)), but have type-specific capsular polysaccharides (CPS) that distinguish the major serotypes (types Ia, Ib, II, III, IV, V, VI, VII, and VIII). The structure of each of these various type-specific capsular polysaccharides has been characterized (19, 20, 21, 22, 43, 44, 47). Similarly, *Streptococcus pneumoniae* have a common group antigen (C-substance), but different type-specific capsular polysaccharides. Currently, there are 90 known serotypes of *S. pneumoniae* that are differentiated by their capsular polysaccharide coat (7, 49). Because of outer surface variation, bacterial types (or sub-strains) may be identified and classified according to type-specific antibodies. Thus, methods that can purify cell wall antigenic polysaccharides, either in their native state or as antigenic substructures, efficiently and simply, will greatly aid vaccine development.

Group and type-specific polysaccharides have been successfully used as targets for protective antibodies, where the production of these antibodies is provided by vaccines that stimulate active immunity. The antibodies generated in response to vaccination with vaccines having a type-specific polysaccharide component are also useful for providing passive immunity. Large-scale production of polysaccharides for use in vaccine manufacture requires adequate supplies of purified polysaccharides. Some methods (43, 45) for isolating capsular polysaccharides from certain bacterial cells rely on treatment of cells with the enzyme mutanolysin. Mutanolysin cleaves the bacterial cell wall which frees the cellular components. This procedure also involves treating cell lysate with additional enzymes to degrade proteins and nucleic acids. Other reported methods (50) for isolating polysaccharides from microorganisms rely on treatment of cells with hot phenol. Phenol separates the polysaccharides into the aqueous layer. The aqueous layer is concentrated by ultrafiltration to yield crude polysaccharide fractions which are then purified by chromatography. These methods are laborious and costly, as the necessity to eliminate toxic molecules associated with the cell wall (e.g., lipid A endotoxin, lipoteichoic acids and muramyl peptides) requires the use of expensive enzymes and complicated chromatography to degrade and remove toxins. More efficient, higher yielding and simpler means of obtaining purified polysaccharides are desirable.

Yet another effective method for isolating capsular polysaccharides (described in U.S. Pat. No. 6,248,570) relies upon base hydrolysis to extract CPS from cell wall components. This method allows for the degradation and removal of nucleic acids, proteins, and toxins from polysaccharides without the laborious and costly use of enzymes. Although this base hydrolysis method affords greater simplicity, efficiency, safety, and general applicability in relation to other previously reported methods, an even greater improvement of this method has been achieved in the present invention.

Advantages of the present invention include at least one of (1) simplicity, (2) an increase in molecule yield, (3) scalability (i.e., large scale production), (4) the purified polysaccharide can retain or be returned to its native antigenic form, and (5) DNA, RNA, and toxins are degraded in the hydrolysis steps and therefore are not present in appreciable amounts in the final product produced according to this invention.

SUMMARY OF THE INVENTION

In some embodiments, purification of polysaccharides from a stock comprising the polysaccharides and cellular components may be achieved by the following method. The method entails contacting the stock with a first reagent to form a first mixture. The first reagent is an acid or base, and the pH of the first mixture is in the range 0-6 or in the range of 9-15. A separated composition is formed by separating the polysaccharide from at least some of the cellular components. The separated composition comprises the polysaccharide and a residual amount of the cellular components. The separated composition is contacted by a second reagent to form a second mixture. The second reagent is a base, and the pH of the second mixture is in the range of 9-15. A purified composition is formed from the purification of the polysaccharide from at least some of the residual amount of the cellular components.

In some embodiments, purification of polysaccharides from a stock comprising the polysaccharides and cellular components may be achieved by the following method. The method entails a contacting the stock with a first reagent to form a first mixture. The first reagent comprises a base and a reducing agent, and the pH of the first mixture is in the range of 9-15. A separated composition is formed by separating of the polysaccharide from at least some of the cellular components. The purified polysaccharide is recovered after the separation step.

The step of contacting the stock with a first reagent is sometimes referred to herein as the "first step hydrolysis". The step of contacting the separated composition with a second reagent is sometimes referred to herein as the "second step hydrolysis". These designations are made for clarity and should not be taken as limiting in any manner.

Non-limiting examples of the use of the invention include making compositions of purified polysaccharides, polysaccharide—polypeptide conjugates, pharmaceutical compositions, diagnostic kits, and antibodies. The antibodies can be reactive with the original source of the polysaccharides, and they may be cross-reactive with other organisms.

In some embodiments, a polysaccharide conjugate vaccine can be made using the following method. Purified polysaccharide is obtained using the methods described above. The polysaccharide is conjugated to a polypeptide, thereby making the vaccine. In some embodiments, an adjuvant is added to the vaccine. In some embodiments, the conjugation is accomplished by reductive amination.

DETAILED DESCRIPTION OF THE INVENTION

Figure 1:
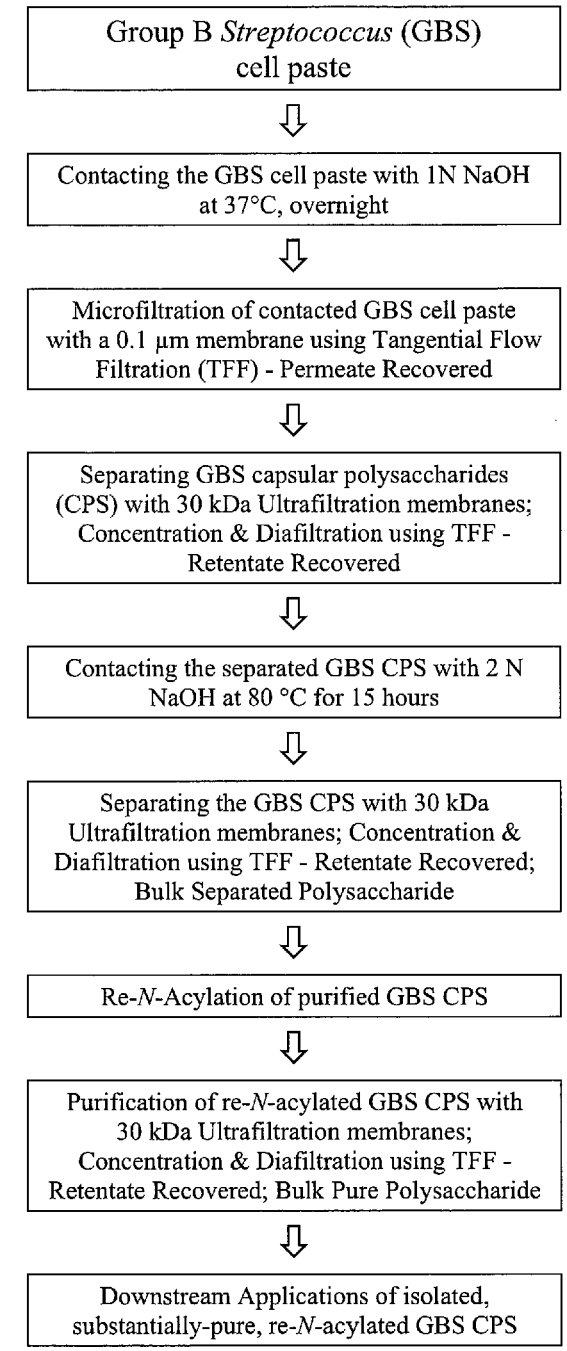
FIG. 1 presents an experimental schematic of the present invention used to isolate group B *streptococcus* (GBS) capsular polysaccharides (Example 1)

The methods of the invention can be used to extract polysaccharides from cellular components with significant yields. For a comparison of yields, see Example 1. In some embodiments, the method may also advantageously be used to breakdown high molecular weight polysaccharides. Furthermore, in some embodiments, the methods of the invention allow for the optional use of convenient membrane-filtration methods to separate and purify polysaccharides from contaminants such as proteins and nucleic acids. Previously, substantially pure polysaccharides were typically obtained by using low-throughput and complicated precipitation and column chromatographic techniques. The ability to use membrane-filtration methods to separate and purify extracted polysaccharides is desirable, as membrane-filtration is a simple, high throughput, and scalable technology that maintains high yields of purified polysaccharide.

Purification of polysaccharides from a stock comprising the polysaccharides and cellular components can be achieved, according to some embodiments this invention, by a two-step hydrolysis method. The two-step hydrolysis method entails a first step hydrolysis using base or acid, where the base or acid reagent can result in the hydrolysis of one or more bonds between a polysaccharide and cellular components, for example, a microbial cell wall. These base-labile or acid-labile bonds can be phosphodiester bonds linking the polysaccharide to a peptidoglycan and/or phosphodiester bonds linking a polyrhamnose to the peptidoglycan. The hydrolysis of bonds between polysaccharides and cell wall components can detach the polysaccharide from the cell wall component. The first step hydrolysis is followed by separation step, which, for example, can separate polysaccharide from non-attached cellular components, for example cell wall components, proteins, nucleic acids and lipids to create a separated composition. The separation composition comprises the polysaccharide and a residual amount of the cellular components. A second step hydrolysis can then be performed on the separated composition that can hydrolyze any remaining bonds between polysaccharides and cell wall components, and/or at least partially degrade non-desired proteins and nucleic acids. The second step hydrolysis is followed by separation, and optional N-acylation and purification.

In some embodiments, the polysaccharides can be isolated using more than two hydrolysis steps. Although two hydrolysis steps can be sufficient to obviate the need of using chromatography for isolating substantially pure polysaccharides, more than two hydrolysis steps may result in increased yield and purity, and can be determined using methods described in this invention. In some embodiments, three hydrolysis steps are used, each followed by a separation step. In some embodiments, four hydrolysis steps are used, each followed by a separation step. In some embodiments, more than four hydrolysis steps can be used.

In some embodiments, the purifications of polysaccharides can be accomplished without purified nucleases and/or purified proteases added in the reagent for one, two, and/or all the hydrolysis steps. In these embodiments, the reaction mixture may still contain nucleases and/or proteases through impurities and/or through their presence in the stock comprising the polysaccharide.

In some embodiments, only one hydrolysis step is required. In these methods, the first reagent comprises a base and a reducing agent. The reducing agent can, for example, help protect the polysaccharide during the hydrolysis step.

In some embodiments, the pH range for detaching polysaccharides from other cellular components is 9-14, for example 10-13; from 11-13; or 12. Hydrolysis can be accomplished at temperatures from 2° C. to 100° C.; for example, 4° C.-100° C., 20° C.-100° C., 30° C.-100° C., 40° C.-100° C., 25° C.-90° C., 30° C.-80° C. 34° C.-41° C., or 37° C. The temperature ranges whose lower end is greater than or equal to 25° C. may result in increased yields. A second-step hydrolysis can be accomplished at conditions preferably stronger than the hydrolysis conditions used in the first-step hydrolysis procedure, such that proteins, endotoxins, and nucleic acids are at least partially degraded. In some embodiments, the second step hydrolysis can occur at a temperature that is 10-90° C. hotter than the first step (e.g., at least 10, 20, 30, 40, 50, 60, or 70° C. hotter, but not more than 90° C. hotter). In some embodiments, maximum temperature during the second-step hydrolysis is 10-90° C. hotter than maximum temperature during the first-step hydrolysis (e.g., at least 10, 20, 30, 40, 50, 60, or 70° C. hotter, but not more than 90° C. hotter). For example, the maximum temperature during which the separated composition is contacted with the second reagent is 30° C.-90° C. hotter than the maximum temperature during which the stock is contacted with the first reagent. In some embodiments, the second step can last 1-45 hours longer than the first step (e.g., at least 1, 5, 10, 15, 20, 25, 30, 35, or 40 hours longer, but not more than 45 hours longer). In some embodiments, the pH of the second step mixture can be 0.1-5 units further in absolute value from pH 7 than the first step mixture (e.g., at least 0.1, 0.2, 0.3, 0.4, 0.5, 1, 1.3, 1.5, 2, 2.3, 2.5, 3, 3.3, 3.5, 4, or 4.5 units further, but not more than 5 units further). In some embodiments, the normality of base in the second mixture can be 0.25-4 N larger than the normality of the acid or base used in the first mixture (e.g., at least 0.25, 0.5, 0.75, 1, 1.5, 2, 3.5, 3, or 3.5 N larger, but not more than 4 N larger). For example, the second-step hydrolysis can be conducted at 40° C.-90° C. hotter than the first-step hydrolysis, with a second mixture having a base normality that is 0.5-4 N larger than the normality of the acid or base in the first mixture. For example, the second-step hydrolysis conditions can be conducted at 80° C. for 15-48 hours (depending on the polysaccharide to be purified) with a final concentration of 2 N NaOH. Such conditions are typically sufficient to significantly degrade both nucleic acids and proteins, whose fragments can then be easily removed by filtration. In some embodiments, the two-step hydrolysis method can result in the breakdown of high molecular weight polysaccharides, which can be particularly and ultimately useful in products made by the method.

Starting Materials:

The sources of polysaccharides to be purified according to this invention are varied. Sources include bacteria, archaea, and eukaryotes. In multi-cellular organisms, the source can be a part of the whole organism (e.g., cancer cells or cancerous cells).

Further examples of organisms include bacterial pathogens such as *Aeromonas hydrophila* and other species (spp.); *Bacillus anthracis*; *Bacillus cereus*; Botulinum neurotoxin producing species of *Clostridium*; *Brucella abortus*; *Brucella melitensis*; *Brucella suis*; *Burkholderia mallei* (formally *Pseudomonas mallei*); *Burkholderia pseudomallei* (formerly *Pseudomonas pseudomallei*); *Campylobacter jejuni*; *Chlamydia psittaci*; *Clostridium botulinum*; *Clostridium botulinum*; *Clostridium perfringens*; *Coccidioides immitis*; *Coccidioides posadasii*; *Cowdria ruminantium* (Heartwater); *Coxiella burnetii*; Enterovirulent *Escherichia coli* group (EEC Group) such as *Escherichia coli*—enterotoxigenic (ETEC), *Escherichia coli*—enteropathogenic (EPEC), *Escherichia coli*—O157:H7 enterohemorrhagic (EHEC), and *Escherichia coli*—enteroinvasive (EIEC); *Ehrlichia* spp. such as *Ehrlichia chaffeensis*; *Francisella tularensis*; *Legionella pneumophilia*; *Liberobacter africanus*; *Liberobacter asiaticus*; *Listeria monocytogenes*; miscellaneous enterics such as *Klebsiella, Enterobacter, Proteus, Citrobacter, Aerobacter, Providencia*, and *Serratia*; *Mycobacterium bovis*; *Mycobacterium tuberculosis*; *Mycoplasma capricolum*; *Mycoplasma mycoides* ssp *mycoides*; *Peronosclerospora philippinensis*; *Phakopsora pachyrhizi*; *Plesiomonas shigelloides*; *Ralstonia solanacearum* race 3, biovar 2; *Rickettsia prowazekii*; *Rickettsia rickettsii*; *Salmonella* spp.; *Schlerophthora rayssiae var zeae*; *Shigella* spp.; *Staphylococcus aureus*; *Streptococcus*; *Synchytrium endobioticum*; *Vibrio cholerae* non-O1; *Vibrio cholerae* O1; *Vibrio parahaemolyticus* and other *Vibrios*; *Vibrio vulnificus*; *Xanthomonas oryzae*; *Xylella fastidiosa* (citrus variegated chlorosis strain); *Yersinia enterocolitica* and *Yersinia pseudotuberculosis*; and *Yersinia pestis*.

Further examples of organisms include fungi such as: *Aspergillus* spp.; *Blastomyces dermatitidis*; *Candida*; *Coccidioides immitis*; *Coccidioides posadasii*; *Cryptococcus neoformans*; *Histoplasma capsulatum*; Maize rust; Rice blast; Rice brown spot disease; Rye blast; *Sporothrix schenckii*; and wheat fungus.

Further examples of organisms include parasitic protozoa and worms, such as: *Acanthamoeba* and other free-living amoebae; *Anisakis* sp. and other related worms *Ascaris lumbricoides* and *Trichuris trichiura*; *Cryptosporidium parvum*; *Cyclospora cayetanensis*; *Diphyllobothrium* spp.; *Entamoeba histolytica*; *Eustrongylides* sp.; *Giardia lamblia*; *Nanophyetus* spp.; *Shistosoma* spp.; *Toxoplasma gondii*; and *Trichinella*.

Further examples of sources include cancer cells or cancerous tissue such as small cell lung carcinoma, neuroblastomas, breast cancer, colon carcinoma, and the like. These cancers cells or cancerous tissues may be mammalian, for example, human, mouse, dog, cat, goat, monkey, or cow.

Non-limiting examples of gram-positive bacteria for use according to this invention are *Streptococci, Staphylococci, Enterococci, Bacillus, Corynebacterium, Listeria, Erysipelothrix*, and *Clostridium*. Non-limiting examples of gram-negative bacteria for use with this invention include *Haemophilus*, (e.g., *Haemophilus influenzae*), *Neisseria* (e.g., *Neisseria meningitidis*) and *Escherichia*, (e.g., *Escherichia coli*).

A polysaccharide desired for purification may be associated with a cellular component, such as a cell wall. Association with the cell wall means that the polysaccharide is a component of the cell wall itself, and/or is attached to the cell wall, either directly or indirectly via intermediary molecules, or is a transient coating of the cell wall (for example, certain bacterial strains exude capsular polysaccharides, also known in the art as 'exopolysaccharides').

In some embodiments, the polysaccharide extracted from bacteria can be a capsular polysaccharide, a sub-capsular polysaccharide, or lipopolysaccharide. In some embodiments, the polysaccharide can be a capsular polysaccharide.

In some embodiments, the polysaccharide can be the group-specific polysaccharide of group A *streptococcus* (GAS), a sub-capsular polysaccharide.

In some embodiments, the polysaccharide can be extracted from group B *streptococcus* (GBS). In some embodiments, the polysaccharide can be a type-specific CPS extracted from GBS types Ia, Ib, II, III, IV, V, VI, VII and/or VIII. In some embodiments, the polysaccharide can be the CPS extracted from GBS types Ia, Ib, II, III and V.

In some embodiments, the polysaccharide can be the group polysaccharide from group C *streptococcus* (GCS), a sub-capsular polysaccharide.

In some embodiments, the polysaccharide can be extracted from *S. pneumoniae*. In some embodiments, CPS can be extracted from *S. pneumoniae* types 3 and 14.

In some embodiments, the polysaccharide can be extracted from *Neisseria* or *Escherichia* bacteria. In some embodiments, the polysaccharide can be extracted from *Neisseria meningitidis* types B, C, Y or W135 or *Escherichia coli* K1.

In some embodiments, one polysaccharide is purified. In some embodiments, a plurality of polysaccharides are co-purified from one or more sources.

As used herein, the term "stock" refers to the starting material that comprises a polysaccharide to be purified. Exemplary stocks are supernatants, conditioned media, homogenized cells, or cell pellets. If exopolysaccharides (capsular polysaccharides that are exuded from a bacterium into a supernatant or media) are the desired polysaccharide, an exemplary stock can be a concentrated supernatant, formed by separating the cells by centrifugation or microfiltration and concentrating the supernatant, typically 10-15 fold. In some embodiments, the stock is a supernatant or conditioned medium that has been concentrated so that polysaccharides are present at a concentration of 5-20 mg/mL. If the polysaccharide of interest is attached to a cell wall, then exemplary stocks are pelleted or homogenized cells.

First-Step Hydrolysis:

According to this invention, polysaccharides are extracted by contacting a stock with a first reagent, an acid or a base reagent. Without being bound by theory, it is believed that a covalent bond is broken between the polysaccharide and the cellular components, such as the cell wall, (or between the polysaccharide and intermediary molecules linking the polysaccharide to the cellular components), where the cellular component may itself be a polysaccharide, protein, or lipid, for example. Other types of bonds may include, but are not limited to, ionic bonds and bonds formed by Van der Waals forces. The bond connecting the polysaccharide and the cell wall component may be a 'direct' bond between the polysaccharide and the cell wall component, or an 'intervening' or 'indirect' bond that result in the attachment of the polysaccharide to the cell wall component. The chemical reaction that results in the breaking of the bond is either a base or acid hydrolysis reaction.

Generally, group B *Streptococcus* polysaccharides having sialic acid bonds are cleavable by acid, but not to base. However, capsular polysaccharides containing phosphodiester linkages are cleaved mainly by base, and to a lesser degree by acid. For example, *Haemophilus influenzae* type b and some pneumococcal capsular polysaccharides, such as, 6A, 6B, 18, and 23. Meningococcal A and pneumococcal type 19 are examples of some capsular polysaccharides that are cleaved by both acid and base.

First Reagent Compositions

In some embodiments, the first reagent comprises one or more of a variety of bases. Non-limiting examples of bases which may be used according to this invention comprise a compound chosen from NaOH, KOH, LiOH, $NaHCO_3$, $Na_2CO_3$, $K_2CO_3$, KCN, $Et_3N$, $NH_3$, $H_2N_2H_2$, NaH, NaOMe, NaOEt and KOtBu. In some embodiments, bases such as NaOH, KOH, LiOH, NaH, NaOMe or KOtBu can be used in a range of 0.5 N-10 N (e.g., 0.5N-5 N, 0.5 N-2 N, or 0.8-1.5 N) In some embodiments, bases such as $NaHCO_3$, $Na_2CO_3$, $K_2CO_3$ and KCN can be used in concentrations as high as their solubilities permit. In some embodiments, organic bases such as triethylamine ($Et_3N$) may be used at medium to high concentrations, for example, ranging from 1 N through 7 N (e.g., 2 N-4 N), as long as there is an agent such as water or alcohol to effect the hydrolysis. Bases such as ammonia ($NH_3$) or hydrazine ($H_2NNH_2$) can be used at nearly any concentration including 100%. Solvents such as water, alcohols (preferably $C_1$-$C_4$), dimethylsulfoxide, dimethylformamide, or mixtures of these and other organic solvents may be used. Base solutions for hydrolysis comprising water can also be used.

In some embodiments, the pH of the first reagent can be in the range of 9-15. For example, the pH of the first reagent can be in the range of any of 10-15, 10-14, 11-14, or 12-14. In some embodiments, a mixture of the stock and the first reagent have a pH in the range of 9-14; for example, the mixture can have a pH in the range of any of 9-13, 10-13, or 11-13. In some embodiments, the pH of the mixture is near 12.

In some embodiments, the first reagent comprises one or more of a variety of acids. Non-limiting examples of acids which may be used according to this invention comprise a compound chosen from HCl, $H_3PO_4$, citric acid, acetic acid, nitrous acid, and sulfuric acid.

In some embodiments, the pH of the first reagent can be in the range of 0-6. For example, the pH of the first reagent can be in the range of any of 0-5, 0-4, 0-3, 1-2. In some embodiments, a mixture of the stock and the first reagent have a pH in the range of 0-6; for example, the mixture can have a pH in the range of any of 0-5, 1-5, 2-5, 3-5, or 4-5. In some embodiments, the pH of the mixture is near 4.

The first reagent can optionally comprise additional materials, such as salts (e.g., NaCl, or KCl), oxidizing agents (e.g., $H_2O_2$, $O_3$, or hypochlorite), reducing agents comprising boron (including, e.g., $NaBH_4$, $NaCNBH_3$, lithium tri-sec-butylborohydride, or $NaBH(OCOCH_3)_3$), other reducing agents (including, e.g., lithium aluminum hydride, dithiothreitol, or β-mercaptoethanol), enzymes (including, e.g., proteases or nucleases), chelators (including, e.g., EDTA or EGTA), and surfactants (nonionic, zwitterionic, anionic or cationic type). In some embodiments, surfactants may be useful in the subsequent filtration step. In some embodiments, the reducing agent can avoid the potential degradation of the polysaccharide by the so-called "peeling" caused by, for example, β-elimination of an adjacent sugar residue linked on the third carbon of the reducing end of the polysaccharide.

In some embodiments, the first reagent comprises a base and a reducing agent. In some embodiments, the base is in the range of 0.5 N-5 N and the reducing agent is in the range of 0.03 mM-300 mM. For example, the base can have a concentration in the range of 0.5 N-2 N and the reducing agent can have a concentration in the range of 0.3 mM-30 mM. Exemplary first reagents include a base and sodium borohydride. In some embodiments, the base concentration is in the range of 0.5 N-5 N and the sodium borohydride concentration is in the range of 0.03 mM-300 mM. For example, the base concentration can be in the range of 0.5 N-2 N and the sodium borohydride concentration is in the range of 0.3 mM-30 mM. In some embodiments, the base is chosen from NaOH, LiOH and KOH.

Use

In some embodiments, the stock can be 0.1-300 g of cell paste per liter of the first reagent. For example, the stock can be 0.5-200 g of cell paste per liter of the first reagent. For example, the stock can be 1-100 g of cell paste per liter of the first reagent. For example, the stock can be 5-150 g of cell paste per liter of the first reagent. For example, the stock can be 20-100 g of cell paste per liter of the first reagent. In some embodiments, the stock is concentrated supernatants or conditioned media into which a concentrated first reagent (e.g., 10 N NaOH) is added to achieve a less concentrated mixture (e.g., determined by the mixture's pH or determined by the concentration of a component of the first reagent in the mixture: e.g., 10 N NaOH diluted to 1 N NaOH).

Hydrolysis can be accomplished at temperatures from 2° C. to 100° C.; for example, 4° C.-100° C., 20° C.-100° C., 30° C.-100° C., 40° C.-100° C., 25° C.-90° C., 30° C.-80° C., 34° C.-41° C., or 37° C. The temperature ranges whose lower end is greater than or equal to 25° C. may result in increased yields. In some embodiments, the mixture is incubated for 1-48 hours to allow reactions to occur. For example, the incubation can last 1, 2, 3, 4, 5, 6, 7, 8, 9, 10, 12, 14, 15, 16, 18, 20, 24, 36, or 48 hours or any time in between. In some embodiments, the mixture is agitated during the incubation. In some embodiments, the mixture is not agitated during the incubation. In some embodiments, a first-step hydrolysis is accomplished at 37° C. with agitation at a final concentration of 1 N NaOH using a 15-18 hour incubation.

Exemplary uses of acidic first reagents include the hydrolysis of the group-specific polysaccharide of group A or group C *streptococcus*, (e.g., the GAS or GCS sub-capsular polysaccharide). In some embodiments for such polysaccharides, the first reagent comprises 0.1 N HCl, sodium nitrate (NaNO$_2$), or acetate buffers at a pH of 4-5. In some embodiments for such polysaccharides, the pH of the mixture is near 4. In some embodiments, the first-step acid hydrolysis may be accomplished at room temperature at a final concentration of 0.1 N HCl with the mixture's pH near 4. Other acid concentrations may also be used, depending on factors such as amount of stock in the mixture, the desired pH of the mixture, and the interaction of the particular acid with the stock. Acetate buffers pH 4-5, sodium nitrite (NaNO$_2$) may be used as well at temperatures ranging from 25° C. to 60° C.

In some embodiments for the purification of group B *Streptococcus*, group Y meningococcus, and group W-135 meningococcus capsular polysaccharides, 1-100 grams, (e.g., 1-75 grams) of cell paste can be contacted with 750 mL of 1 N NaOH and 100 mg of sodium borohydride. This reaction mixture can be shaken at a speed of 125 rpm, for example, for 16 hours at 37° C.

First-Step Separation:

Unless stated otherwise, the aspects of the invention indicated below in the First-Step Separation also fully apply to all other separation and purification steps of the invention.

The extracted polysaccharides present in the base or acid hydrolysis reagent may be separated from impurities resulting from the other cellular components based on charge, hydrophilicity, affinity, solubility or stability, or size. Non-limiting examples of separation techniques include ammonium sulfate precipitation, chromatography, and membrane-filtration (including tangential flow membrane filtration). In embodiments utilizing chromatography for separation, exemplary methods include ion-exchange (cationic or anionic), affinity chromatography, hydrophilic-interaction, hydrophobic-interaction, size-exclusion and gel-permeation (see U.S. Pat. No. 6,248,570).

In some embodiments, the separation can be conducted by membrane-filtration, which includes, but is not limited to, methods such as single pass, dead-end, direct flow filtration (DFF), and crossflow or tangential flow filtration (TFF). According to the invention, filtration is based on the principle of separating molecules according to size using a semi-permeable membrane of a defined range of pore sizes. It is known to those skilled in the art that combinations of filtration methods and membrane types may be used in separation.

According to the invention, membrane-filtration is the separation of cellular components effected by polymeric or inorganic membranes. Within the art, there are four commonly accepted categories of membranes defined by the size of the material they remove from the carrier liquid. Methods of sequentially filtering through membranes from the smallest to largest pore size are Reverse Osmosis (RO), Nanofiltration (NF), Ultrafiltration (UF), and Microfiltration (MF).

Filtration with the above-mentioned membranes separates molecules according to their molecular weight by using membranes with specific pore sizes. For example, separation with RO membranes that have pore sizes less than 0.001 micrometers is intended to separate molecules that have a molecular weight less than 200 Daltons. Filtration with NF membranes that have pore sizes from 0.001-0.008 micrometers, inclusive, is intended to separate molecules that have a molecular weight from 200 Daltons to 15 kilodaltons (kDa) inclusive. Filtration with UF membranes that have pore sizes from 0.005-0.1 micrometers, inclusive, is intended to separate molecules that have a molecular weight from 5 kDa-300 kDa, inclusive. Filtration with microfiltration membranes that have pore sizes from 0.05-3.0 micrometers, inclusive, is intended to separate molecules that have a molecular weight from 100 kDa-3000 kDa and larger.

According to this invention, membrane-filtration can separate extracted polysaccharides from other cellular components based on size exclusion by utilizing membranes that have a particular Molecular Weight Cut-Off (MQWCO) that is determined by the pore size of the membrane. The MWCO, also called Nominal Molecular Weight Limit (NMWL) or Nominal Molecular Weight Cut-Off (NMWCO), is the kilodalton size designation for the filtration by membranes. The MWCO is defined as the molecular weight of the molecule that is 90% retained by the membrane. Because, for example, molecules of the same molecular weight can have significantly different shapes, the MWCO is not an exact metric, but is nevertheless a useful metric and is commonly employed by filter manufacturers. Both hydrophobic as well as hydrophilic membranes may be used in the present invention. Such membranes may be used as flat sheets or in a spirally wound configuration. Hollow fibers may also be used. In relation to compositions of UF membranes, any number of potential membrane materials may be used including, but not limited to, regenerated cellulose, polyether sulfone (which may or may not be modified to alter its inherent hydrophobicity), polyvinylidene fluoride, and ceramic and metal oxide aggregates. Many polyether sulfone UF membranes can withstand a pH range of 0.5-13, and temperatures ranging up to 85° C. Materials for MF membranes include everything used for UF membranes, as well as polycarbonate, polypropylene, polyethylene and even PTFE (TEFLON®).

In some embodiments, the reaction mixture after the first hydrolysis step can be filtered for the separation of large cellular debris from smaller cellular components to prevent the cellular debris from interfering with the proceeding separation and purification steps that involve the use of membranes or chromatography. In these embodiments, the permeate comprises the polysaccharide and is recovered. In some embodiments, the reaction mixture after the first hydrolysis can be filtered with microfiltration membranes that have pore sizes between 0.05-3.0 micrometers (e.g., filters having a MWCO of 500 kDa-3000 kDa, and larger). In some embodiments, the reaction mixture after the first hydrolysis can be filtered with microfiltration membranes that have pore sizes between 0.05-0.5 micrometers (e.g., 0.1-0.2 μm). In some embodiments, the reaction mixture after the first hydrolysis step is filtered with a 0.05-3.0 micrometer (μm) polyethersulfone hollow fiber filter module.

In some embodiments, a membrane can be used in a separation step having a MWCO in the range of 5 kDa-300 kDa. For example, the MWCO can be 5 kDa-200 kDa, 30 kDa-100 kDa, 10 kDa-60 kDa, or 50 kDa-200 kDa. In these embodiments, the retentate comprises the polysaccharide and can be recovered.

In some embodiments, both the 500 kDa-3000 kDa and the 5 kDa-300 kDa filtering steps are performed. For example, the permeate from the 500 kDa-3000 kDa filtration can then be filtered with a 5 kDa-300 kDa membrane and the final retentate recovered.

In some embodiments, tangential flow filtration can act to both diafilter (the fractionation process that washes smaller molecules through a membrane and leaves larger molecules of interest in the retentate) and concentrate a reaction mixture. According to the invention, diafiltration can be either discontinuous or continuous diafiltration. In discontinuous diafiltration, the solution is concentrated, and the lost volume is replaced by a new buffer. In continuous diafiltration, the solution volume is maintained by the inflow of new buffer solution while the old buffer solution is removed.

In some embodiments, the separation and purification of polysaccharides can be performed by tangential flow filtration methods using ultrafiltration membranes.

In some embodiments, chromatography is not used in the separation of the polysaccharides from cellular components.

In some embodiments, an ultrafiltration membrane can be used to separate GBS CPS in the first separation step, where the MWCO of the membrane can be 5 kDa-100 kDa. For example, the MWCO of the ultrafiltration membrane can be 15 kDa-50 kDa. For example, the MWCO of the ultrafiltration membrane used to separate GBS CPS can be 30 kDa.

In some embodiments, a separation step uses an ultrafiltration membrane having a MWCO of 5 kDa-200 kDa. The UF membrane can be used to separate *Neisseria Meningitidis* types B, C, Y, or W135; *E. coli* K1, group C *Streptococcus* sub-CPS; or group A *Streptococcus* sub-CPS in the first separation step. In some embodiments, the MWCO of the ultrafiltration membrane used to separate group Y meningococcus capsular polysaccharide (GYMP) and group W-135 meningococcus capsular polysaccharide (GWMP) can be 100 kDa.

Second-Step Hydrolysis:

The polysaccharides from the first step separation are contacted with a second reagent, a base reagent, to form a second mixture. Without being bound by theory, the second-step hydrolysis can be useful for at least one of (1) detaching any remaining cellular, particularly cell wall, components attached to polysaccharides while maintaining the natural structure or native antigenicity of the polysaccharide, and (2) degrading other cellular component contaminants (such as proteins and nucleic acids). In some embodiments, this second step of hydrolysis can obviate the need for complicated chromatographic methods to obtain substantially pure polysaccharides.

Second Reagent Compositions

The second reagent comprises one or more of a variety of bases. Non-limiting examples of bases which may be used according to this invention comprise a compound chosen from NaOH, KOH, LiOH, $NaHCO_3$, $Na_2CO_3$, $K_2CO_3$, KCN, $Et_3N$, $NH_3$, $H_2N_2H_2$, NaH, NaOMe, NaOEt and KOtBu. In some embodiments, bases such as NaOH, KOH, LiOH, NaH, NaOMe or KOtBu can be used in a range of 1 N-10 N (e.g., 1 N-6 N, or 2-5 N). In some embodiments, bases such as $NaHCO_3$, $Na_2CO_3$, $K_2CO_3$ and KCN can be used in concentrations as high as their solubilities permit. In some embodiments, organic bases such as triethylamine ($Et_3N$) may be used at medium to high concentrations, for example, ranging from 1 N through 7 N (e.g., 2 N-5 N), as long as there is an agent such as water or alcohol to effect the hydrolysis. Bases such as ammonia ($NH_3$) or hydrazine ($H_2NNH_2$) can be used at nearly any concentration including 100%. Solvents such as water, alcohols (preferably $C_1$-$C_4$), dimethylsulfoxide, dimethylformamide, or mixtures of these and other organic solvents may be used. Base solutions for hydrolysis comprising water can also be used.

In some embodiments, the pH of the second reagent can be in the range of 9-15. For example, the pH of the second reagent can be in the range of any of 10-15, 10-14, 11-14, or 12-14. In some embodiments, the second mixture can have a pH in the range of 9-15; for example, the second mixture can have a pH in the range of any of 10-15, 10-14, 10-13, 11-14, or 11-13.

The second reagent can optionally comprise additional materials, such as salts (e.g., NaCl, or KCl), oxidizing agents (e.g., $H_2O_2$, $O_3$, or hypochlorite), reducing agents comprising boron (including, e.g., $NaBH_4$, $NaCNBH_3$, lithium tri-sec-butylborohydride, or $NaBH(OCOCH_3)_3$), other reducing agents (including, e.g., lithium aluminum hydride, dithiothreitol, or β-mercaptoethanol), enzymes (including, e.g., proteases or nucleases), chelators (including, e.g., EDTA or EGTA), and surfactants (nonionic, zwitterionic, anionic or cationic type). In some embodiments, surfactants may be useful in the subsequent filtration step.

In some embodiments, the second reagent comprises a base and a reducing agent. In some embodiments, the base is in the range of 1 N-10 N and the reducing agent is in the range of 0.03 mM-300 mM. For example, the base can have a concentration in the range of 2 N-6 N and the reducing agent can have a concentration in the range of 0.3 mM-30 mM. Exemplary first reagents include a base and sodium borohydride. In some embodiments, the base concentration is in the range of 1 N-10 N and the sodium borohydride concentration is in the range of 0.03 mM-300 mM. For example, the base concentration can be in the range of 2 N-6 N and the sodium borohydride concentration is in the range of 0.3 mM-30 mM. In some embodiments, the base is chosen from NaOH, LiOH and KOH.

Use

Hydrolysis can be accomplished at temperatures from 20° C. to 100° C.; for example, 30° C.-100° C., 37° C.-100° C., 40° C.-100° C., 50° C.-95° C., 60° C.-90° C., 70° C.-90° C., or 80° C. In some embodiments, the mixture is incubated for 3-72 hours to allow reactions to occur. For example, the incubation can last 4, 5, 6, 7, 8, 9, 10, 12, 14, 15, 16, 18, 20, 24, 36, 48, 60, or 72 hours or any time in between. In some embodiments, the mixture is agitated during the incubation. In some embodiments, the mixture is not agitated during the incubation.

In some embodiments, the second-step hydrolysis, when compared to the first-step hydrolysis, is accomplished using at least one of (1) a higher temperature, (2) a pH whose absolute value is further from 7, (3) a higher molarity reagent, and (4) a longer incubation time. In some embodiments, the second step hydrolysis can occur at a temperature that is at least 10, 20, 30, 40, 50, 60, or 70° C. hotter than the first step. In some embodiments, the second step can last 1, 5, 10, 15, 20, 25, 30, 35, 40, or 45 hours longer than the first step, or any amount of time between 1 and 45 hours longer. In some embodiments, the pH of the second step mixture can be 0.1, 0.2, 0.3, 0.4, 0.5, 1, 1.3, 1.5, 2, 2.3, 2.5, 3, 3.3, 3.5, 4, 4.5, or 5 units further in absolute value from pH 7 than the first step mixture, or any amount between 0.1 and 5. In embodiments using these stronger conditions in the second-step hydrolysis, other cellular components, such as proteins and nucleic acids, can be degraded more efficiently than in the first-step hydrolysis.

One exemplary second-step hydrolysis uses 1-2 N NaOH at 37° C. for 12-48 hours. Another exemplary second-step hydrolysis uses 2 N NaOH at 80° C. for 15-48 hours.

In some embodiments for the second hydrolysis for GBS CPS can be conducted under conditions of a final concentration of 2 N NaOH at 80° C. for 16-18 hours, which are stronger conditions than exemplary conditions for the first hydrolysis for GBS CPS (final concentration of 1 N NaOH at 37° C. for 16 hours).

In some embodiments for the second hydrolysis for GYMP can be conducted under conditions of a final concentration of 2 N NaOH at 80° C. for 48 hours, which are stronger conditions than exemplary conditions for the first hydrolysis for GYMP (final concentration of 1 N NaOH at 37° C. for 16 hours).

In some embodiments for the second hydrolysis step for GWMP may be conducted under conditions of a final concentration of 2 N NaOH at 80° C. overnight (as used herein, "overnight" means 15-18 hours), which are stronger conditions than exemplary conditions for the first hydrolysis step for GWMP (final concentration of 1 N NaOH at 37° C. for 16 hours).

Second-Step Separation:

The extracted polysaccharide from the second-step hydrolysis can be similarly separated as the first-step separation from impurities resulting from the cellular components by separation techniques such as, but not limited to, chromatography and membrane-filtration. Non-limiting examples of the chromatographic separation methods are ion-exchange (cationic or anionic), hydrophilic-interaction, hydrophobic-interaction, or gel-permeation chromatography. An exemplary method is tangential flow filtration using an ultrafiltration membrane.

In some embodiments, chromatography is not used in the second-step separation of polysaccharides. In some embodiments, chromatography is not used in the process of purifying polysaccharides.

In some embodiments, the second-step separation (e.g., for GBS CPS) is conducted with ultrafiltration membranes having a MWCO of 20-50 kDa (e.g., 30 kDa).

In some embodiments, some large proteins (larger than 300 kDa for example) are resistant to degradation by the hydrolysis steps (for instance, see Examples 2 and 3). To eliminate these proteins, the mixture from the second-hydrolysis step is loaded onto ultrafiltration or microfiltration membranes having a high MWCO, for example, 200-400 kDa (e.g., 300 kDa). The permeate is then collected, as the retentate holds the large proteins resistant to degradation. The permeate may be concentrated and diafiltered prior to loading on another membrane, for example, an ultrafiltration membrane with a MWCO from 5-100 kDa, preferably 5-50 kDa, and most preferably 30 kDa, to eliminate small molecular weight impurities, such as nucleic acids and degraded proteins.

In some embodiments, the second-step separation (e.g., for GYMP or GWMP) is conducted first with a 300 kDa UF Membrane in order to remove large proteins resistant to base-hydrolysis degradation. The resultant permeate is then loaded onto a 30 kDa UF Membrane to remove small molecular weight impurities. The retentate from the 30 kDa UF membrane-filtration step is used for proceeding steps.

Optional N-Acylation:

After finally separating the polysaccharide from the other cellular components, free amino groups, from which native acetyl groups may have been removed, may be reacylated, as the hydrolysis procedure may deacetylate the polysaccharides. Varying the acylating reagent and reaction conditions allows the practitioner to control the extent to which the amino groups are reacylated. The acylation reagents and their breakdown products can be small in size in comparison to the reacylated polysaccharide and may therefore be separated from the polysaccharide by a size-exclusion method, for example, gel-permeation chromatography or membrane-filtration. Alternatively, the difference in polarity or charge may be exploited with chromatography to purify the polysaccharide.

The separated polysaccharides may be optionally reacylated to the extent desired by using a variety of acylating agents. Non-limiting examples of acylating agents are acetic anhydride, acetyl chloride, pentafluorophenyl acetate, 4-nitrophenyl acetate (51). The preferred acylation method relates to mixing the separated polysaccharides with an acylating agent, at concentrations of 0.5 M-2 M (e.g., 0.7 M-1 M), in order to reacylate the polysaccharide's free amino groups, thus regenerating the native polysaccharide structure. See, e.g., U.S. Pat. Nos. 5,969,130; 5,576,002; 4,727,136; and 4,356,170.

Purification After Optional N-acylation:

In some embodiments, re-acylated polysaccharides can be purified using chromatographic purification or membrane-filtration. For example, ion-exchange (cationic or anionic), hydrophobic-interaction, hydrophilic-interaction, gel-permeation chromatography, direct flow filtration, or tangential flow filtration may all be used to effect separation of the re-acylated polysaccharides from reaction components. An exemplary method utilizes either gel-permeation chromatography on Superdex (cross-linked agarose and dextran) or tangential flow filtration with ultrafiltration membranes which removes residual contaminants and affords purified polysaccharides. In some embodiments utilizing gel-permeation chromatography on Superdex, the chromatography can use Superdex 200 PG which has a fractionation range (MW) for dextrans of 1,000-100,000 with flow rates that can be from 0.1 mL/min to 10 mL/min using PBS as eluant. In some embodiments utilizing tangential flow filtration, ultrafiltration membranes can be used having, for example, a MWCO of 5 kDa-100 kDa (e.g., 5 kDa-50 kDa, or 5 kDa-30 kDa).

Purity

The degree of purity of the purified polysaccharide is measured by the percentage of sialic acid by weight in a dry composition as estimated by a modified microscale orcinol assay (35). In some embodiments, the purity of the purified polysaccharide is 80%-100%. Exemplary purities include 85%-100%, 90%-100%, 94%-100%, 95%-100%, and over 99%.

In some embodiments, purity can be characterized by the amount of nucleic acid as detected by UV photometry at 260 nm, as expressed as a mass percentage. In some embodiments, the purity of the purified polysaccharide can be <5% nucleic acid, for example, <4%, <3%, <2%, <1%, or <0.5% nucleic acid.

In some embodiments, purity can be characterized by the mass percentage of protein in the purified polysaccharide, as determined by the Bradford procedure (9) using Pierce (Rockford, Ill.) Commie Plus reagent and human IgG as standard. In some embodiments, the purity of the purified polysaccharide can be <5% protein, for example, <4%, <3%, <2%, <1%, <0.5%, <0.1%, or <0.05% protein.

In some embodiments, the purity of the purified polysaccharide can be <3% nucleic acids and <1% protein. In some embodiments, the purity of the purified polysaccharide can be <1% nucleic acids and <1% protein. In some embodiments, the purity of the purified polysaccharide can be <1% nucleic acids, <1% protein, and 90%-100% polysaccharide.

In some embodiments, the purity of the purified polysaccharide can be at least sufficient to be used in a vaccine in treating mammals (e.g., humans), and for linking to proteins to make conjugates of polysaccharides and proteins.

Conjugate Molecules

In some embodiments, the polysaccharides of this invention may be used to elicit antibody responses to a variety of microorganisms, including gram-negative and gram-positive bacteria, in an individual either alone or when conjugated to another immunogenic molecule such as a polypeptide or protein, such as carrier proteins, such as a carrier protein. Conjugation of the polysaccharide to the polypeptide converts the immune response to the polysaccharide which is typically T-cell independent to one which is T-cell dependent. Accordingly, the size of the polypeptide is preferably one which is sufficient to cause the conversion of the response from T-cell independent to T-cell dependent. It may by useful to use smaller polypeptides for the purpose of providing a second immunogen.

Non-limiting examples of polypeptides useful for conjugation include carrier proteins, keyhole limpet hemacyanin (KLH), bovine serum albumin (BSA), ovalbumin (OVA), rabbit serum albumin (RSA), tetanus toxoid, diphtheria toxoid, pneumolysoid, outer membrane protein, viral glycoprotein, as well as variants, fragments, and mimetics thereof. Fragment C of tetanus toxin (TTc) and a recombinant TTc (rTTc) may be used as carriers for polysaccharides. Fragment C (TTc) is the carboxyl-terminal portion of tetanus toxin comprising amino acids of about 865-1315 as reported by International Publication WO 2005/000346. Recombinant expression of Fragment C is reported in U.S. Pat. No. 5,443,966. One skilled in the art is knowledgeable in selecting an immunogenic molecule with which to conjugate to the polysaccharide.

Any mode of conjugation may be employed to conjugate the polysaccharide component with the peptide. A preferred method is described in U.S. Pat. Nos. 4,356,170 and 4,902,506, which describe the introduction of terminal aldehyde groups into polysaccharides via oxidative cleavage of vicinal diols and coupling the aldehyde groups to the peptide amino groups by reductive amination.

It is to be understood, however, that the conjugate molecules of the invention are not limited to those produced via reductive amination. Thus, the vaccines may also be produced by conjugating the polysaccharide with a peptide using any linking method known to those skilled in the art such as an adipic dihydrazide spacer, as described by Schneerson, R. et al. (55) and in U.S. Pat. No. 4,644,059, or, for example, binary spacer technology as described by Marburg, S. et al. (56).

The purified polysaccharides prepared according to this invention may be used to produce conjugate molecules where the peptide is linked to the polysaccharide through one or more sites on the polysaccharide. Accordingly, conjugate molecules prepared according to this invention, with respect to the protein component, may be monomers, dimers, trimers, and more highly cross-linked molecules wherein the polysaccharide cross-links together multiple proteins.

Vaccines

In some embodiments, a polysaccharide vaccine can be made. The polysaccharides can be purified by the methods described above. These polysaccharides may be used as antigens to generate antibodies that are reactive against the polysaccharides and hence reactive against the organism from which the polysaccharide was isolated. More specifically, these embodiments provide for the preparation of polysaccharide vaccines, either alone or conjugated to a polypeptide, which can, for example, protect humans or animals against infection, typically by that strain of bacteria, yeast, or protozoa from which the polysaccharide was isolated. In certain cases, the polysaccharide used with this invention may induce the production of antibodies which are cross-reactive with other pathogenic microorganisms thereby producing protection against infection by these other microorganisms. In certain cases, the polysaccharide use with this invention may be useful in treating or preventing cancer.

In addition, vaccines prepared with polysaccharides purified according to this invention may also include adjuvants, such as alum, aluminum hydroxide, stearyl tyrosine, and Freund's, for example, that are useful in activating the immune system to confer immunity to a host against the immunogen in a prophylactic manner (for example, see U.S. Pat. No. 5,773,007). In some embodiments, adjuvants can be chosen from CD14 receptor agonists, Toll-like receptor agonists, QS21, MF59, monophosphoryl lipid A (MPL).

The vaccines of this invention may provide active or passive immunity. Vaccines for providing active immunity comprise the purified polysaccharide of the invention. Preferably, the purified polysaccharide is a capsular polysaccharide.

In some embodiments, a polysaccharide conjugate vaccine can be made. The polysaccharides can be purified by the methods described above. The purified polysaccharide can be conjugated to a polypeptide, as described in the conjugate molecule section above.

Non-limiting examples of vaccines that may be prepared from polysaccharides purified according to this invention include: Group A *Streptococcal* vaccines (see U.S. Pat. No. 5,866,135), Group B *Streptococcal* type II and III vaccines (see U.S. Pat. Nos. 5,302,386 and 6,284,884), and Group B *Neisseria Meningitidis* vaccines (see U.S. Pat. Nos. 5,969,130; 5,902,586; 5,969,130; 5,683,699; 5,576,002; 5,811,102). Further, the polysaccharides purified according to this invention may also be used in combination vaccines.

Antibodies

The techniques for polysaccharide hydrolysis and separation, as described above, provide for the production of abundant amounts of the isolated polysaccharides of the invention. This facilitates the generation of antibodies reactive against the polysaccharide. One embodiment of the invention provides a method for producing substantially pure or isolated polysaccharides which are capable of eliciting the production of antibodies. Depending on the polysaccharides used, the resultant antibodies may be bactericidal, bacteriostatic, fungicidal, or protozoacidal, and protective for animals against infection by microorganisms containing antigens which are cross-reactive with the polysaccharide used to elicit the antibody response.

Antibodies specific for the isolated polysaccharide or immunogenic portion thereof, may be generated using methods that have long been known and conventionally practiced in the art. Such antibodies may include, but are not limited to, polyclonal, monoclonal, chimeric, single chain Fab fragments and fragments produced by an Fab expression library. Neutralizing antibodies (i.e., those which inhibit dimer formation) are especially preferred for therapeutic use.

For the production of antibodies, various hosts including, goats, rabbits, sheep, rats, mice, horses, cows, humans, and others, may be immunized by injection with the isolated polysaccharide, or any fragment or conjugates thereof, which has immunogenic properties. Depending on the host species, various adjuvants may be used to increase the immunological response. Non-limiting examples of suitable adjuvants include Freund's (complete or incomplete), mineral gels such as aluminum hydroxide or silica, and surface active substances, such as lysolecithin, pluronic polyols, polyanions, peptides, oil emulsions, KLH, and dinitrophenol. Adjuvants typically used in humans include bacilli Calmette Guérin (BCG) and *Corynebacterium parvumn*.

Monoclonal antibodies to the isolated polysaccharide, or immunogenic fragments thereof, may be prepared using any technique which provides for the production of antibody molecules by continuous cell lines in culture. These include, but are not limited to, the hybridoma technique, phase display, the human B-cell hybridoma technique, and the EBV-hybridoma technique (G. Kohler et al., 1975, *Nature*, 256:495-497; D. Kozbor et al., 1985, *J. Immunol. Methods*, 81:31-42; R. J. Cote et al., 1983, *Proc. Natl. Acad. Sci. USA*, 80:2026-2030; and S. P. Cole et al., 1984, *Mol. Cell Biol.*, 62:109-120). The production of monoclonal antibodies is well known and routinely used in the art.

According to one method, cultures of hybridoma cell lines are used (52). Monoclonal antibodies directed against the polysaccharide may be human monoclonal antibodies, chimeric monoclonal antibodies, or humanized monoclonal antibodies made by techniques that are commonly known in the art. According to one approach, chimeric monoclonal antibodies may be generated to have a non-human (e.g., mouse) antigen-binding domain combined with a human constant region (53). Humanized antibodies may be generated according to the procedures of U.S. Pat. No. 5,585,089 to Queen, et al. The isolated polysaccharide, peptide or fragment thereof, may comprise a single epitope or antigenic determinant or multiple epitopes. Portions of the isolated polysaccharide may be fused with those of another protein, such as KLH, and antibodies are produced against the chimeric molecule.

In addition, techniques developed for the production of chimeric antibodies, the splicing of mouse antibody genes to human antibody genes to obtain a molecule with appropriate antigen specificity and biological activity, may be used (S. L. Morrison et al., 1984, *Proc. Natl. Acad. Sci. USA*, 81:6851-6855; M. S. Neuberger et al., 1984, *Nature*, 312:604-608; and S. Takeda et al., 1985, *Nature*, 314:452-454). Alternatively, techniques described for the production of single chain antibodies may be adapted, using methods known in the art, to produce polysaccharide-specific single chain antibodies. Antibodies with related specificity, but of distinct idiotypic composition, may be generated by chain shuffling from random combinatorial immunoglobulin libraries (D. R. Burton, 1991, *Proc. Natl. Acad. Sci. USA*, 88:11120-3). Antibodies may also be produced by inducing in vivo production in the lymphocyte population or by screening recombinant immunoglobulin libraries or panels of highly specific binding reagents as disclosed in the literature (R. Orlandi et al., 1989, *Proc. Natl. Acad. Sci. USA*, 86:3833-3837 and G. Winter et al., 1991, *Nature*, 349:293-299).

Antibodies directed against the polysaccharide may be purified by any of the techniques that are well known in the art including, but not limited to immunoabsorption or immunoaffinity chromatography or other chromatographic methods (e.g., HPLC). Antibodies may also be purified as immunoglobulin fractions from serum, plasma, or cell culture medium.

Antibody fragments, which contain specific binding sites for the isolated polysaccharide, may also be generated, including but not limited to Fab, Fab', $F(ab')^2$, Facb, Fv, ScFv, Fd, VH, and VL. Antibody molecules of this invention may be intact immunoglobulin molecules, substantially intact immunoglobulin molecules, or those portions of an immunoglobulin molecule, for example Fab fragments, that contain the antigen binding site. Fragments of antibodies directed against the polysaccharide may be generated by any of the techniques that are commonly known in the art (54). For example, such fragments include, but are not limited to, $F(ab')^2$ fragments which can be produced by pepsin digestion of the antibody molecule and Fab fragments which can be generated by reducing the disulfide bridges of the $F(ab')^2$ fragments. Alternatively, Fab expression libraries may be constructed to allow rapid and easy identification of monoclonal Fab fragments with the desired specificity (W. D. Huse et al., 1989, *Science*, 254.1275-1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve measuring the formation of complexes between the isolated polysaccharide and its specific antibody. A two-site, monoclonal-based immunoassay utilizing monoclonal antibodies reactive with two non-interfering polysaccharide epitopes is preferred, but a competitive binding assay may also be employed (Maddox, supra).

Another aspect of the invention relates to a method for inducing an immunological response in a mammal which comprises inoculating the mammal with the isolated polysaccharide, or a fragment thereof, adequate to produce antibody and/or T cell immune response to protect said animal from infections such as bacterial, fungal, protozoan and viral infections, particularly infections caused by HIV-1 or HIV-2. Yet another aspect of the invention relates to a method of inducing immunological response in a mammal which comprises, delivering the isolated polysaccharide via a vector directing expression of its polynucleotide in vivo in order to induce such an immunological response to produce antibody to protect the mammal from diseases.

Pharmaceutical Compositions

The pharmaceutical compositions of this invention may comprise the polysaccharide or conjugate molecules comprising polysaccharides and pharmacologically acceptable carriers such as saline, dextrose, glycerol, ethanol, or the like. In another embodiment, the pharmaceutical composition comprises another immunogenic moiety, such as a peptide, or compositions comprising antibodies elicited by one of the polysaccharides of this invention. The pharmaceutical composition may also comprise adjuvants to enhance the immunological response of the recipient. Such adjuvants may be aluminum based such as alum or long chain alkyl adjuvants such as stearyl tyrosine (see U.S. Pat. No. 5,773,007, filed Sep. 17, 1990; European Pat., EP 0 549 617 131; Moloney et al. U.S. Pat. No. 4,258,029). See also Jennings, et al. (U.S. Pat. No. 5,683,699) and Paoletti, et al. (58). These pharmaceutical compositions are particularly useful as vaccines.

For eliciting passive immunity, the pharmaceutical composition may be comprised of polyclonal antibodies or monoclonal antibodies, or their derivatives, or Fragments thereof, as described above. The amount of antibody, fragment, or derivative is a therapeutically or prophylactically effective amount as determined by standard clinical techniques.

In some embodiments, antibodies directed against the polysaccharide of the invention may be used as a pharmaceutical preparation in a therapeutic or prophylactic application in order to confer passive immunity from a host individual to another individual (i.e., to augment an individual's immune response against gram-negative or gram-positive bacteria or to provide a response in immuno-compromised or immuno-depleted individuals, including AIDS patients). Passive transfer of antibodies is known in the art and may be accomplished by any of the known methods. According to one method, antibodies directed against the polysaccharide or conjugates thereof of this invention are generated in an immunocompetent host ("donor") animal, harvested from the host animal, and transfused into a recipient individual. For example, a human donor may be used to generate antibodies reactive against the polysaccharide or polysaccharide conjugate of this invention. The antibodies may then be administered in therapeutically or prophylactically effective amounts to a human recipient in need of treatment, thereby conferring resistance in the, recipient against bacteria which are bound by antibodies elicited by the polysaccharide component (57).

In some embodiments, this invention can provide a method for producing substantially pure polysaccharides which are capable of eliciting the production of antibodies. Depending on the polysaccharides used, the resultant antibodies may be bactericidal, fungicidal, or protozoacidal, and protective for animals against infection by microorganisms containing antigens which are cross-reactive with the polysaccharide used to elicit the antibody response.

The pharmaceutical preparations of this invention may be introduced to in individual by methods known to be effective in the art. Intradermal, intraperitoneal, intravenous, subcutaneous, intramuscular, oral, and intranasal are among, but not the only, routes of introduction.

The compositions of the invention may comprise standard carriers, buffers, or preservatives commonly known to those in the art which are suitable for vaccines including, but not limited to, any suitable pharmaceutically and physiologically acceptable carrier, such as physiological saline or other injectable liquids. Additives customary in vaccines may also be present, for example stabilizers, such as lactose or sorbitol, and adjuvants to enhance the immunogenic response, such is aluminum phosphate, hydroxide, or sulphate and stearyl tyrosine. The vaccines produced according to this invention may also be used as components of multivalent vaccines which elicit an immune response against a plurality of infectious agents.

Vaccines of the present invention are administered in amounts sufficient to elicit production of antibodies as part of an immunogenic response. Dosages may be adjusted based on the size, weight, or age of the individual receiving the vaccine. The antibody response in an individual can be monitored by assaying for antibody titer or bactericidal activity and boosted if necessary to enhance the response. Typically, a single dose for an infant is about 10 micrograms (µg) of conjugate vaccine per dose or 0.5 µg-20 µg/kilogram. Adults receive a dose of 0.5 µg-20 µg/kilogram of the conjugate vaccine. For a CPS vaccine, a typical dose is about 25 µg of each individual CPS per dose. That is, a vaccine against group B streptococcus would comprise 25 µg of each of the CPS from each of the nine serotypes. Doses ranging from 2 µg-15 µg of each of the CPS are commonly appropriate for polysaccharide conjugate vaccines.

Diagnostic Kits

In another embodiment, the polysaccharides of this invention, derivatives, or fragments thereof, may be used to produce safer diagnostic kits that do not incorporate toxins such as pneumolysin toxin but can still indicate the presence of antibodies directed against gram-negative or gram-positive bacteria, or other microorganisms. The presence of such antibodies can indicate prior exposure to the pathogen and predict individuals who may be resistant to infection. The diagnostic kits may comprise at least one of the polysaccharides of this invention, derivatives, or fragments thereof, and suitable reagents for the detection of an antibody reaction when the modified polysaccharides, derivatives, or fragments thereof, are mixed with a sample that contains antibodies directed against gram-negative or gram-positive bacteria, or other microbes. An antibody reaction may be identified by any of the methods described in the art, including but not limited to an ELISA, fluorescence, calorimetric, chemiluminescence, or an electrochemiluminescence assay. Such knowledge is important, and can, for example, avoid unnecessary vaccination.

Alternatively, the diagnostic kit may further comprise a solid support magnetizable bead, or plastic matrix, and at least one of the polysaccharides of this invention, derivatives, or fragments thereof.

In some cases, it may be preferred that the polysaccharides, derivatives, or fragments thereof, are labeled. Labeling agents are well known in the art. For example, labeling agents include, but are not limited to, radioactivity, chemiluminescence, bioluminescence, luminescence, or other identifying and/or detectable "tags" for convenient analysis. Body fluids or tissues samples (e.g., blood, serum, saliva) may be collected and purified and applied to the diagnostic kit. The polysaccharides, derivatives, or fragments thereof may be purified or non-purified and may be composed of a cocktail of molecules.

Solid matrices are known in the art and are available, and include, but are not limited to, polystyrene, polyethylene, polypropylene, polycarbonate, or any solid plastic material polymer in the shape of test tubes, beads, macroparticles, microparticles, dip-sticks, plates, chip or the like. Additionally matrices include, but are not limited to membranes, 96-well microtiter plates, test tubes, and Eppendorf tubes. In general such matrices comprise any surface where a ligand-binding agent can be attached or a surface which itself provides a ligand attachment site.

EXAMPLES

The following examples are presented to illustrate the invention but are in no way to be construed as limitations on the scope of the invention. It will be recognized by those skilled in the art that numerous changes and substitutions may be made without departing from the spirit and purview of the invention.

Bacteria Strains, Growth Media, and Cultivation Conditions

Type Ib group B streptococcal strain H36b (ATCC 12401) was obtained from American Type Culture Collection (Rockville, Md.). The other strains used, 090 (type Ia), 18RS21 (type II), M781 (type III), and CJ11 (type V), were kindly provided by D. L. Kasper, Harvard Medical School. *Neisseria meningitidis* types B, C, Y and W135 were kindly provided by Carl Frasch at CBER, FDA and *Escherichia coli* KI was kindly provided by Willie Vann at CBER, FDA.

Each of the bacterial strains was grown individually in a dialysate (10,000 MWCO), Pellicon cassette system (Millipore Corp.; Bedford, Mass.) of 3.5% Columbia broth (Difco Laboratories, Inc.; Detroit, Mich.) supplemented with 6% glucose. A 150 mL seed culture grown for 8 h in a shaking Erlenmeyer flask at 37° C. was used to inoculate a Bioflo IV 20-liter fermentor (New Brunswick Scientific Co.; Edison, N.J.) filled with 14 liters of broth (vide supra). The fermentation culture was maintained at 37° C., continually adjusted to pH 7.1 with the addition of 10 N NaOH and aerated at 1.5 L/min. The cells were harvested after 17 h by microfiltration through a MiniKros 0.1 µm porosity, hollow-fiber cartridge (Microgon, Inc.; Laguna Hills, Calif.). The culture supernatant was sterilely maintained at 4° C. until further processed. Final cell pellets were obtained by centrifugation of separated cells at 9000 rpm in a Sorvall GSA rotor (DuPont Clinical & Instruments Div.; Wilmington, Del.) for 50 min.

Polysaccharides can also be purified from culture supernatants. After removal of cells, the broth is concentrated and diafiltered according to the procedure described in the general method for producing polysaccharides.

Molar Mass Determination

Absolute molar mass distributions of polysaccharides were determined by analytical gel permeation chromatography (GPC) with detection by inline multiangle laser-light-scattering photometry and differential refractometry (GPC-MALLS/RI). This method was performed on a liquid chromatography system consisting of a Jasco PU-980 HPLC pump (Easton, Md.), a Rheodyne model 7125 injection valve (Cotati, Calif.), and a Superose 6 HR 10/30 column equilibrated with PBS and with a flow rate of 0.5 mL/min. The mobile phase was prepared in ultra-high purity water (Stephens Scientific; Riverdale, N.J.) and filtered through a 25 mm diameter in-line filter (Millipore) equipped with a Millipore type GV 0.22-mm membrane. Polysaccharide samples (1-2 mg) were dissolved at a concentration of 10 mg/mL in the mobile phase, and the resulting solutions were centrifuged for 2 to 3 minutes at 14,000 rpm in a microcentrifuge to remove particulates before injection. Column effluents were directly analyzed with an in-line Dawn E eighteen Angler-light-scattering photometer (Wyatt Technology Corp.; Santa Barbara, Calif.) coupled to a Hewlett-Packard model 1047A differential refractometer. The analog signal output of the refractometer was connected to the DAWN E through an auxiliary input channel. Light-scattering data was acquired and processed with Wyatt's ASTRA 4.73.40 software. Peak area was calculated by the Wyatt software as the summation of the areas of 200-300 trapezoidal divisions, or "slices", over the full range of a peak. From the area thus obtained, the weight-average and number-average molar masses ($M_w$ and $M_n$, respectively) of a polysaccharide eluting in a given peak were calculated. The specific refractive-index increment (dn/dc) was determined for all polysaccharides to be 0.141 mL/g using the on-line HP 1047A refractometer. This value was comparable to values previously obtained for other polysaccharides (7, 8, 40).

One-Dimensional $^1$H NMR Spectra

One-dimensional $^1$H NMR spectra of polysaccharide samples (4-5 mg/mL) in $D_2O$ (Aldrich) were recorded at 500 MHz on a Bruker Instruments AMX 500 spectrometer (Billerica, Mass.). Spectral data were acquired at 50° C., and chemical shifts are referenced to external 3-trimethylsilylpropionate sulfonic acid (Aldrich) in $D_2O$.

Purified Polysaccharide Analysis

Content for the step yield and final purified sample was determined by a modification of the resorcinol assay for quantitative Sialic Acid Analysis (59). Briefly, to 1 mL of sample or control, containing 5 to 50 µg of NeuAc standard or 50 µg/mL of capsular polysaccharide, was added 1 mL of resorcinol reagent (2% resorcinol solution, 0.25 mL of 0.1M $CuSO_4$ solution, 10 mL of deionized water, Quantum Suffice to 100 mL with concentrated HCl). Samples were mixed well and heated in a heating block (VWR) at 110° C. for 25 min. After samples were cooled in watered ice for 5 min, 2 mL of the hydrolysis solution (Butyl AcetateButanol [85/15 (v/v)]) were added to each sample. A 1 mL portion from the organic phase of each sample was transferred to a quartz cuvette and read at 580 nm in a Shimadzu, UV 160U, UV-Visible Recording Spectrophotometer. Purity of final polysaccharide preparations was derived from sialic acid content using the following formula weights: 309 g/mol for terminal NeuAc residue; 1004 g/mol for repeat unit of GBS types Ia, Ib, or III CPS; 1328 g/mol for repeat unit of GBS types II or V CPS.

Protein content was determined for samples containing 20 mg capsular polysaccharide per milliliter in PBS by the Bradford procedure (9) using Pierce (Rockford, Ill.) Commie Plus reagent and human IgG as standard. Nucleic acid content was determined by direct UV photometry at 260 nm. Photometric measurements for these assays were made with a Shimadzu model UV 160U spectrophotometer (Shimadzu Scientific Inst.; Columbia, Md.).

Example 1

Hydrolysis and Isolation of Group B *Streptococcus* (GBS) Capsular Polysaccharides FIG. 1 presents an experimental schematic of an embodiment of the invention used in this example.

First-Step Hydrolysis Using Base:

750 mL of 1 N NaOH was added to 75 g GBS cell paste immediately after the centrifugation step as stated previously, forming a cell suspension. Contents were transferred to a 2 L bottle and 100 mg of sodium borohydride was optionally added to the cell suspension. The reaction mixture was shaken at 125 rpm for 16 hours at 37° C.

Separation by Membrane-Filtration

The overnight cell lysate was diluted 10 fold with deionized (DI) water to a final NaOH concentration of 0.1 N. The diluted cell lysate was clarified by microfiltration using a 0.1 gm polyethersulfone hollow fiber filter module with a surface area of 2000 $cm^2$. The microfiltration module was flushed with DI water to remove any residual storage solution, and was then equilibrated by recirculating diluted cell lysate with the permeate line closed for 10 minutes. The microfiltration was performed at constant feed and permeate rate. Following collection of the permeate (about 90% of the starting volume), the filter was washed twice with 1 L of saline to recover polysaccharide in the retentate.

About 13 L of cell-free permeate from microfiltration was concentrated to about 1 L with a 30 kDa MWCO membrane in a Millipore® Pellicon ultrafilter (UF). The membrane composition is polyethersulfone (Biomax). Constant volumes were diafiltered with first 5 L of 1 M NaCl and then 20 L of DI water. After the concentration and diafiltration steps, the ultrafilter retentate was concentrated to about 70 mL with a labscale Tangential Flow Filtration (TPF) system (Millipore) equipped with a 30 kDa MWCO Biomax membrane.

Second-Step Hydrolysis Using Base:

5 N NaOH was added to the 30 kDa retentate to achieve a final concentration of 2 N NaOH. After the polysaccharide was further extracted at 80° C. for 16-18 hours, the mixture was cooled to less than 50° C. and poured into 10 L of DI water.

Second-Step Separation by Membrane-filtration:

Sodium hydroxide as well as the small molecular weight impurities are removed by 5 L of 1 M NaCl and 20 L of DI water by constant volume diafiltration with a 30 kDa MWCO polyethersulfone (Biomax) membrane, and then concentrated to a minimum volume of around 70 mL with a labscale TFF system equipped with a 30 kDa MWCO Biomax membrane.

Optional Re-N-Acylation:

As the exposure of the polysaccharide to the previously described hydrolysis conditions releases N-acetyl groups from the polysaccharide, the polysaccharide was re-N-acetylated by dropwise addition of acetic anhydride (Aldrich Chemical Co.; Milwaukee, Wis.) to the pooled fractions to a final concentration of 0.8 M. This reaction mixture was stirred at room temperature for 1 hour and maintained at pH 9 with the addition of 5 N NaOH. The pH of the reaction was then increased to 13, and the reaction was continued for an additional 90 minutes. The pH of the reaction was then adjusted to pH 8 with 6 N of hydrochloric acid.

Purification by Membrane-filtration:

The solution containing re-N-acetylated capsular polysaccharide was diafiltered against 5 L of 0.9% NaCl with a labscale TFF system equipped with a 30 kDa MWCO Biomax ultrafiltration membrane to a minimum volume of around 70 mL. The purified capsular polysaccharide was then stored frozen at −70° C., or utilized for downstream applications, for example, the production of antibodies, pharmaceutical compositions, diagnostic kits, conjugate molecules, and vaccines.

Results:

1. Yields of Purified Capsular Polysaccharides:

Table 1 presents a comparison of the capsular polysaccharide yields of various GBS serotypes obtained by using either the method of Example 1 or the '1-step hydrolysis method' as described in U.S. Pat. No. 6,248,570 to Michon, et al. For all serotypes, the capsular polysaccharides were purified from cell pellets. Of the five serotypes tested, the method of the present invention produced greater yields for four serotypes when compared to the 1-step method.

2. Analysis of Purified Capsular Polysaccharides:

For each of the group B streptococcal serotypes studied, nucleic acid levels, as detected by direct UV photometry at 260 nm, did not exceed 0.5% by mass, whereas protein, as assayed by the Bradford method (9) was <1% by mass (Table 2). Purities of all polysaccharides, calculated from their sialic acid content as estimated by a modified resorcinol assay (36), were about 100%. For all polysaccharide preparations obtained by both the method of the present invention and the one-step hydrolysis method, the photometric data indicate that both methods produce highly purified capsular polysaccharides with minimal contamination by proteins or nucleic acids.

3. Molecular Size of Polysaccharides:

In separate analyses, the absolute molar-mass distributions of the polysaccharides were determined by GPC-MALLS/RI. This method allows direct estimation of molar mass of macromolecules, independent of chromatographic parameters such as flow rate and retention volume, and without the necessity of secondary standards whose hydrodynamic properties may vary greatly from the analyte of interest. The utility of GPC-MALLS/RI as a characterization method has been well established for polysaccharides of pharmaceutical interest (7,8,10,17,25). Molar-mass distributions are usually presented as the weight-average molar-mass (Mw) (Table 2).

TABLE 1

Yields of Group B Streptococcal Capsular Polysaccharide

| Serotype | Approximate Yield from Example 1 (mg/L of culture fermentation) | Approximate Yield from 1-Step Hydrolysis Method (see Table 1 of U.S. Pat. No. 6,248,570) (mg/L of culture fermentation) |
|---|---|---|
| Ia | 130 | 79 |
| Ib | 70 | 64 |
| II | 90 | 42 |
| III | 90 | 65 |
| V | 60 | 65 |

TABLE 2

Biochemical and Biophysical Characterization of Purified Group B Streptococcal Capsular Polysaccharides

| Serotype | MW (kg/mol) [MALLS] | Nucleic acid content % | Protein content (%) |
|---|---|---|---|
| Ia (Example 1) | 607 | 0.21 | <0.01 |
| Ia (1-Step Method) | 311 | 0.15 | <0.01 |
| Ib (Example 1) | 219 | 0.08 | 0.90 |
| Ib (1-Step Method) | 218 | 0.33 | <0.01 |
| II (Example 1) | 333 | 0.05 | <0.01 |
| II (1-Step Method) | 289 | 0.12 | <0.01 |
| III (Example 1) | 115 | 0.27 | 0.10 |
| III (1-Step Method) | 108 | 0.10 | <0.01 |
| V (Example 1) | 275 | 0.09 | 0.30 |
| V (1-Step Method) | 179 | 0.17 | 0.09 |

Example 2

Hydrolysis and Isolation of Group Y Meningococcal Capsular Polysaccharides

Figure 2:
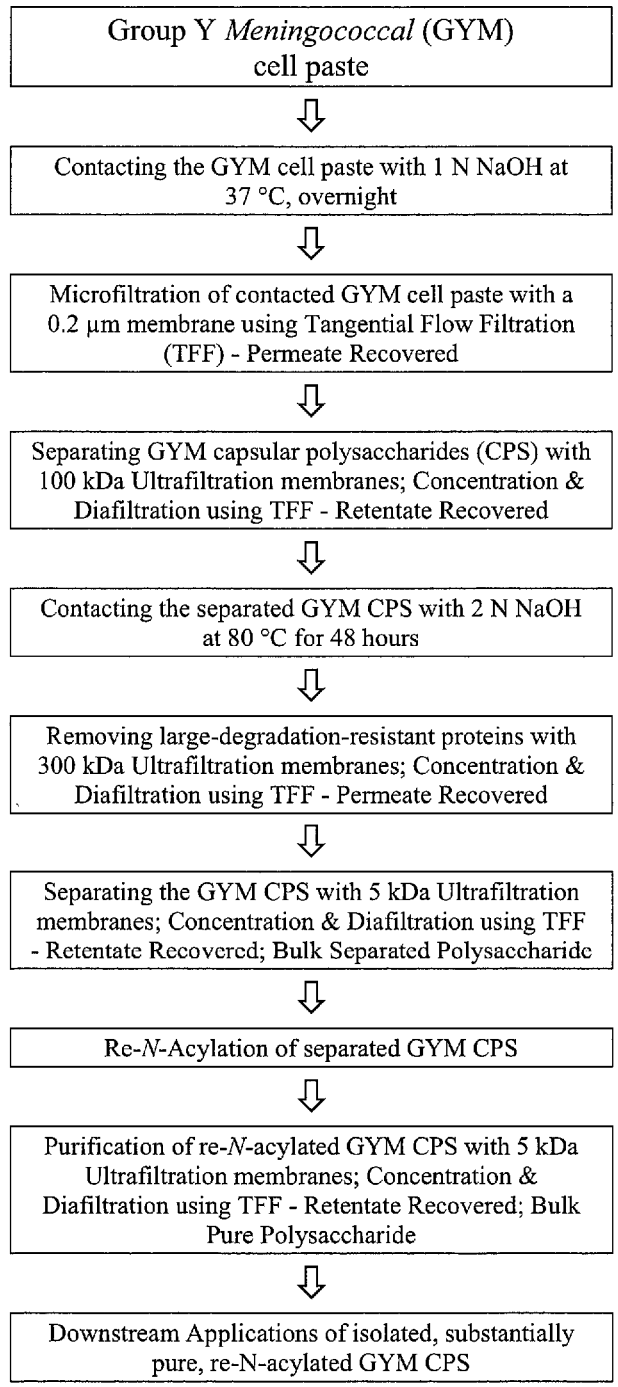
FIG. 2 presents an experimental schematic of the present invention used to isolate group Y *meningococcus* (GYM) capsular polysaccharides (Example 2).
Figure 3:
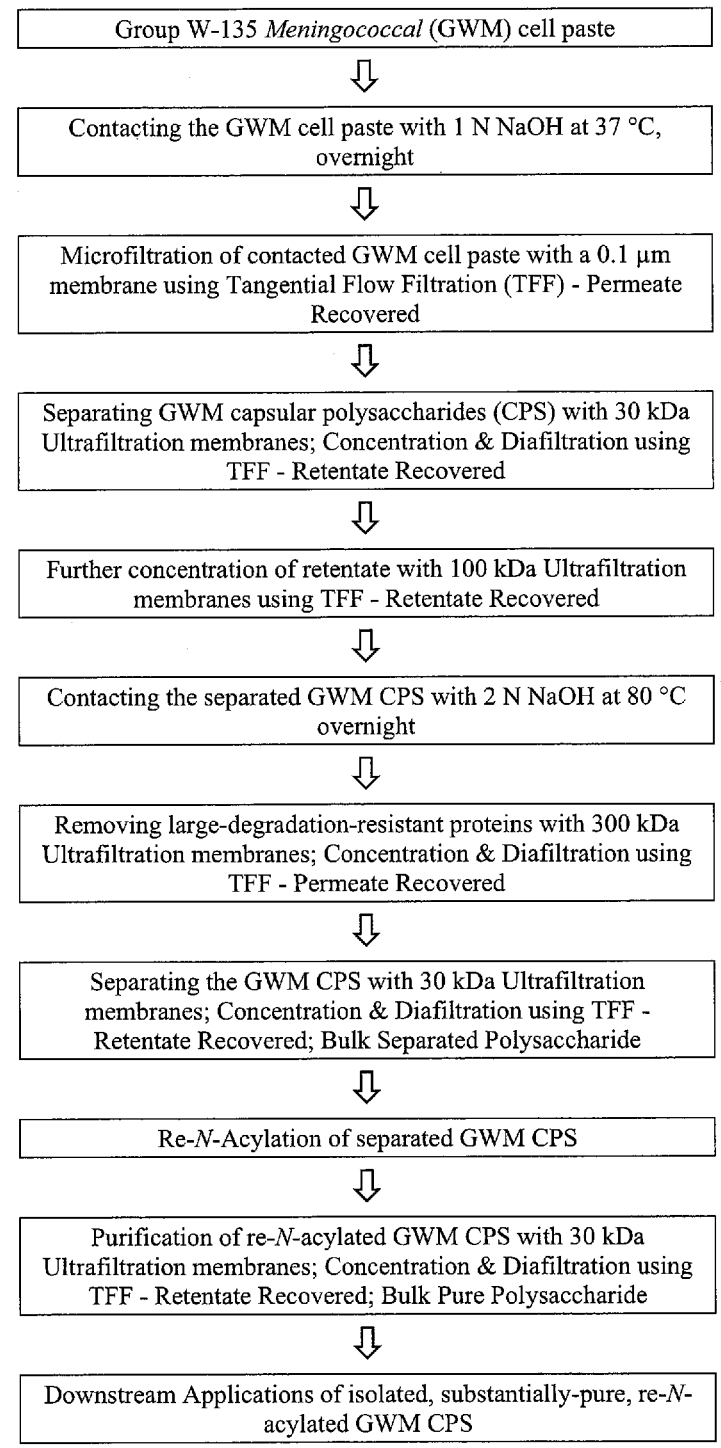
FIG. 3 presents an experimental schematic of the present invention used to isolate group W-135 *meningococcus* (GWM) capsular polysaccharides (Example 3).
Figure 4:
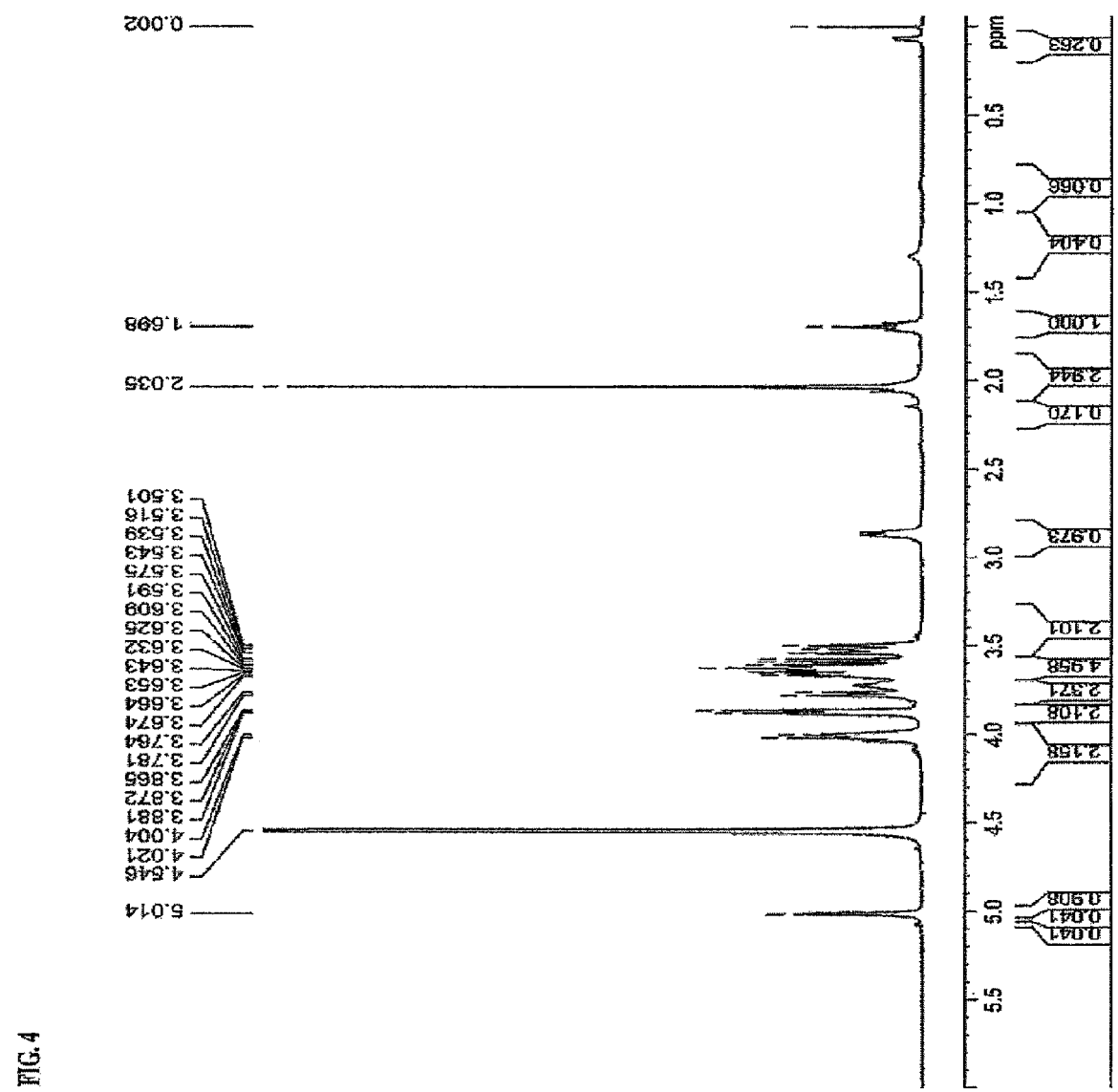
FIG. 4 presents the NMR spectrum of the capsular polysaccharide from group Y *meningococcal* capsular polysaccharides (Example 2).

FIG. 2 presents an experimental schematic of an embodiment of the invention used in this example.

First-Step Hydrolysis Using Base:

750 mL of 1 N NaOH was added to 75 g GYM cell paste immediately after a centrifugation step that pelleted the cells. Contents were transferred to a 2 L bottle and 100 mg of sodium borohydride was added to the cell suspension. The reaction mixture was shaken at 125 rpm for 16 hours-18 hours at 37° C.

Separation by Membrane-filtration:

The overnight cell lysate was diluted 10 fold with deionized (DI) water to a final NaOH concentration of about 0.1 N. The diluted cell lysate was clarified by microfiltration using a 0.1 μm polyethersulfone hollow fiber filter module with a surface area of 2000 cm². The microfiltration module was flushed with DI water to remove any residual storage solution, and was then equilibrated by recirculating diluted cell lysate with the permeate line closed for 10 minutes. The microfiltration was performed at constant feed and permeate rate. Following collection of the permeate (about 90% of the starting volume), the filter was washed twice with 1 L of saline to recover polysaccharide in the retentate.

About 7.5 L of cell-free permeate from microfiltration was concentrated to about 1 L with a 100 kDa MWCO membrane in a Millipore Pellicon ultrafilter (UF). The membrane composition is polyethersulfone (Biomax). Constant volumes were diafiltered with first 5 L of 1 M NaCl and then 20 L of DI water. After the concentration and diafiltration steps, the ultrafilter retentate was concentrated to about 70 mL with a labseale Tangential Flow Filtration (TFF) system (Millipore) equipped with a 100 kDa MWCO Biomax membrane.

Second-Step Hydrolysis Using Base:

5 N NaOH was added to the 100 kDa retentate to achieve a final concentration of 2 N NaOH. After the polysaccharide was further extracted at 80° C. for 48 hours, the mixture was cooled to less than 50° C. and poured into 10 L of DI water.

Second-Step Separation by Membrane-Filtration:

For the purification of GYMP, it was found that some large proteins (larger than 300 kDa) were resistant to degradation by the hydrolysis steps. To eliminate these proteins, the mixture from the second-hydrolysis step was loaded onto a 300 kDa MWCO membrane in a Millipore Pellicon ultrafilter (UF). The permeate was then concentrated to about 1 L with a 5 kDa MWCO membrane in a Millipore Pellicon ultrafilter (UF). The membrane composition is polyethersulfone (Biomax). Constant volumes were diafiltered with first 5 L of 1 M NaCl and then 20 L of DI water. After the concentration and diafiltration steps, the ultrafilter retentate was concentrated to about 70 mL with a labscale Tangential Flow Filtration (TFF) system (Millipore) equipped with a 5 kDa MWCO Biomax membrane.

Optional Re-N-Acylation:

As the exposure of the polysaccharide to the previously described hydrolysis conditions releases N-acetyl groups from the polysaccharide, the polysaccharide was re-N-acetylated by dropwise addition of acetic anhydride (Aldrich Chemical Co., Milwaukee, Wis.) to the pooled fractions to a final concentration of 0.8 M. This reaction mixture was stirred at room temperature for 1 hour and maintained at pH 9 with the addition of 5 N NaOH. The pH of the reaction was then increased to 13, and the reaction was continued for an additional 90 minutes. The pH of the reaction was then adjusted to pH 8 with 6 N of hydrochloric acid.

Purification by Membrane-filtration:

The solution containing re-N-acetylated capsular polysaccharide was diafiltered against 5 L of 0.9% NaCl with a labscale TFF system equipped with a 5 kDa MWCO Biomax ultrafiltration membrane to a minimum volume of around 70 mL. The purified capsular polysaccharide was then stored frozen at −70° C., or can be utilized for downstream applications, for example, the production of antibodies, pharmaceutical compositions, diagnostic kits, conjugate molecules, and vaccines.

Results:

1. Yield of Group Y Meningococcal Capsular Polysaccharide:

The approximate yield of purified group Y meningococcus capsular polysaccharide, using the above method, was 12 mg per liter of bacterial culture.

2. Analysis of Purified GYM Capsular Polysaccharides:

One-dimensional $^1H$ NMR spectrometry of the purified GYM capsular polysaccharide indicated very low levels of contamination. FIG. 4 presents the NMR spectrum (500 MHz) of the purified GYM capsular polysaccharide recorded in $D_2O$ at 50° C. Nucleic acid levels, as detected by direct UV photometry at 260 nm, was 2.46% by mass, whereas protein, as assayed by the Bradford method (9) was not detectable above the lower limit of detection of this assay (1 μg/mL). Purity of the final purification was calculated by the sialic acid content as estimated by a modified microscale orcinol assay (35), was 94%. Thus the spectral and photometric data indicates that the method of hydrolysis and isolation of the present invention allows highly purified GYM capsular polysaccharides with minimal contamination by proteins or nucleic acids.

Example 3

Hydrolysis and Isolation of Group W-135 Meningococcal Capsular Polysaccharides FIG. 3 presents an experimental schematic of an embodiment of the invention used in this example.

First-Step Hydrolysis Using Hydrolysis:

750 mL of 1 N NaOH was added to 75 g of group W-135 meningococcal (GWM) cell paste immediately after a centrifugation step that pelleted the cells. Contents were transferred to two 2 L bottle and 100 mg of sodium borohydride was added to the cell suspension. The reaction mixture was shaken at 150 rpm for 16 hours-18 hours at 37° C.

Separation by Membrane-Filtration:

The overnight cell lysate was diluted 10 fold with deionized (DI) water to a final NaOH concentration of about 0.1 N. The diluted cell lysate was clarified by microfiltration using a 0.2 μm polyethersulfone hollow fiber filter module with a surface area of 2000 $cm^2$. The microfiltration module was flushed with DI water to remove any residual storage solution, and was then equilibrated by recirculating diluted cell lysate with the permeate line closed for 10 minutes. The microfiltration was performed at constant feed and permeate rate. Following collection of the permeate (about 90% of the starting volume), the filter was washed twice with 1 L of saline to recover polysaccharide in the retentate.

About 12 L of cell-free permeate from microfiltration was concentrated to about 1 L with a 30 kDa MWCO membrane in a Millipore Pellicon ultrafilter (UF). The membrane composition is polyethersulfone (Biomax). Constant volumes were diafiltered with first 5 L of 1 M NaCl and then 20 L of DI. water. After the concentration and diafiltration steps, the ultrafilter retentate was concentrated to about 70 mL with a labscale Tangential Flow Filtration (TFF) system (Millipore) equipped with a 100 kDa MWCO Biomax membrane.

Second-Step Hydrolysis Using Hydrolysis:

5 N NaOH was added to the 100 kDa retentate to achieve a final concentration of 2 N NaOH. After the polysaccharide was farther extracted at 80° C. overnight, the mixture was cooled to less than 50° C. and poured into 10 L of DI water.

Second-Step Separation by Membrane-Filtration:

For the purification of group W-135 meningococcal polysaccharide (GWMP), some-large proteins (larger than 300 kDa) were resistant to degradation by the hydrolysis steps. To eliminate these proteins, the mixture from the second-hydrolysis step was loaded onto a 300 kDa MWCO membrane in a Millipore Pellicon ultrafilter (UF). The permeate was then concentrated to about 1 L with a 30 kDa MWCO polyethersulfone (Biomax) membrane in a Millipore Pellicon ultrafilter (UF). Constant volumes were diafiltered with first 5 L of 1 M NaCl and then 20 L of DI water. After the concentration and diafiltration steps, the ultrafilter retentate was concentrated to about 70 mL with a labscale Tangential Flow Filtration (TFF) system (Millipore) equipped with a 30 kDa MWCO Biomax membrane.

Optional Re-N-Acylation:

As the exposure of the polysaccharide to the previously described hydrolysis conditions releases N-acetyl groups from the polysaccharide, the polysaccharide was re-N-acetylated by dropwise addition of acetic anhydride (Aldrich Chemical Co.; Milwaukee, Wis.) to the pooled fractions to a final concentration of 0.8 M. This reaction mixture was stirred at room temperature for 1 hour and maintained at pH 9 with the addition of 5 N NaOH. The pH of the reaction was then increased to 13, and the reaction was continued for an additional 90 minutes. The pH of the reaction was then adjusted to pH 8 with 6 N of hydrochloric acid.

Purification by Membrane-Filtration:

The solution containing re N acetylated capsular polysaccharide was diafiltered against 5 L of 0.9% NaCl with a labscale TFF system equipped with a 30 kDa MWCO Biomax ultrafiltration membrane to a minimum volume of around 70 mL. The purified capsular polysaccharide was then stored frozen at –70° C., or can be utilized for downstream applications, for example, the production of antibodies, pharmaceutical compositions, diagnostic kits, conjugate molecules, and vaccines.

Results:

1. Yield of Group W-135 Meningococcal Capsular Polysaccharide:

The approximate yield of purified group W-135 meningococcal capsular polysaccharide, using the above method, was 25.4 mg per liter of bacterial culture.

2. Analysis of Purified GWM Capsular Polysaccharides:

Nucleic acid levels, as detected by direct UV photometry at 260 nm, was 0.40% by mass, whereas protein, as assayed by the Bradford method (9) was not detectable above the lower limit of detection of this assay (1 μg/mL). Purity of the final purification was calculated by the sialic acid content as estimated by a modified microscale orcinol assay (35), was 95%. Thus, the above photometric data indicates that the method of hydrolysis and isolation of the present invention allows highly purified GWM capsular polysaccharides with minimal contamination by proteins or nucleic acids.

The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. All publications and patents cited in this disclosure are incorporated by reference in their entirety. To the extent the material incorporated by reference contradicts or is inconsistent with this specification, the specification will supersede any such material. The citation of any references herein is not an admission that such references are prior art to the present invention.

Unless otherwise indicated, all numbers expressing quantities of ingredients, reaction conditions, and so forth used in the specification, including claims, are to be understood as being modified in all instances by the term "about." Accordingly, unless otherwise indicated to the contrary, the numerical parameters are approximations and may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Unless otherwise indicated, ranges include the boundary points. For example, "5-14" refers to any value that is greater than or equal to 5 and less than or equal to 14.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

References

1. Anderson, P., G. Peter, R. B. Johnson, L. H. Wetterlow and D. H. Smith. 1972. Immunization of humans with polyribophosphate, the capsular antigen of *Haemophilus influenzae* type b. J. Clin. Invest. 51:39-44.
2. Avery, O. T. and W. F. Goebel. 1931. Chemo-immunological studies on conjugated carbohydrate-proteins V. The immunological specificity of an antigen prepared by combining the capsular polysaccharide of type 3 pneumococcus with foreign protein. J. Exp. Med. 54:43 7-447.
3. Baker, C. J. and D. L. Kasper. 1985. Group B streptococcal vaccines. Rev. Inf. Dis. 7:458-467.
4. Baker, C. J., M. A. Rench, M. S. Edwards, R. J. Carpenter, B. M. Hays and D. L. Kasper. 1988. Immunization of pregnant women with a polysaccharide vaccine of group B *Streptococcus*. N. Engl. J. Med. 319:1180-1185.
5. Baker, C. J., M. A. Rench and D. L. Kasper. 1990. Response to Type III polysaccharide in women whose infants have had invasive Group B streptococcal infection. New EngI. J. Med. 322:1857-1860.
6. Baltimore, R. S., D. L. Kasper and J. Vecchitto. 1979. Mouse protection test for group B *Streptococcus* type III. J. Infect. Dis. 140:81-86.
7. Bednar, B. and J. P. Hennessey. 1993. Molecular size analysis of capsular polysaccharide preparations from *Streptococcus pneumoniae*. Carbohyd. Res. 243:115-130.
8. Beri, R. G., J. Walker, E. T. Reese and J. E. Rollings. 1993. Characterization of chitosans via coupled size-exclusion chromatography and multiple-angle laser light-scattering technique. Carbohyd. Res. 238:11-26.
9. Bradford, M. M. 1976. A Rapid and sensitive method for the quantitation of microgram quantities of protein utilizing the principle of protein-dye binding. Analyt. Biochem. 72:248-254.
10. D'Ambra, A. J., J. E. Baugher, P. E. Concannon, R. A. Pon and F. Michon. 1997. Direct and indirect methods for molar-mass analysis of fragments of the capsular polysaccharide of *haemophilus influenzae* type b. Anal. Biochem. 250:228-236
11. Dick, W. E., Jr. and M. Beurret. 1989. Glycoconjugates of bacterial carbohydrate antigens. p. 48-114. In: J. M. Cruse and R. E. Lewis, Jr., Contributions to microbiology and immunology. S. Karger, Basel.
12. Dillon, H. C., Jr., S. Khare and B. M. Gray. 1987. Group B streptococcal carriage and disease: A 6-year prospective study. J. Pediat. 110:31-36.
13. Goebel, W. F. and O. T. Avery. 1931. Chemo-immunological studies on conjugated carbohydrate-proteins IV. The synthesis of the p-aminobenzyl ether of the soluble specific substance of type 3 pneumococcus and its coupling with protein. J. Exp. Med. 54:431.436.

14. Gold, R., M. L. Lepow, I. Goldschneider, T. L. Draper and E. C. Gotschlich. 1975. Clinical evaluation of group A and group C meningococcal polysaccharide vaccines in infants. J. Clin. Invest. 56:1536-1547.

15. Gold, R., M. L. Lepow, I. Goldschneider and E. C. Gotschlich. 1977. Immune response of human infants to polysaccharide vaccines of Groups A and C *Neisseria meningitidis*. J. Infect. Dis. 136S:S31-S35.

16. Gold, R. M., M. L. Lepow, I. Goldschneider, T. F. Draper and E. C. Gotschlich. 1978. Antibody responses of human infants to three doses of group A *Neisseria meningitides* vaccine administered at two, four and six months of age. J. Infect. Dis. 138:731-735.

17. Hennessey, J. P., B. Bednar and V. Manam. 1993. Molecular size analysis of *Haemophilus influenzae* type b capsular polysaccharide. J. Liq. Chromat. 16:1715-1729.

18. Howard, J. G., G. H. Christie, B. M. Courtenay, E. Leuchars and A. J. S. Davies. 1971. Studies on immunological paralysis. VI. Thymic-independence of tolerance and immunity to type III pneumococcal polysaccharide. Cell. Immunol. 2:614-626.

19. Jennings, H. J., E. Katzenellenbogen, C. Lugowski and D. L. Kasper. 1983. Structure of the native polysaccharide antigens of type Ia and type Ib Group B *Streptococcus*. Biochemistry 22:1258-1263.

20. Jennings, H. J., K.-.G. Rosell and D. L. Kasper. 1980. Structural determination and serology of the native polysaccharide antigen of type III group B *Streptococcus*. Can. J. Biochem. 58:112-120.

21. Jennings, H. J., K.-.G. Rosell and D. L. Kasper. 1980. Structure and serology of the native polysaccharide antigen of type Ia group B *Streptococcus*. Proc. Nat. Acad. Sci. USA. 77:2931-2935.

22. Jennings, H. J., K.-.G. Rosell, E. Katzenellenbogen and D. L. Kasper. 1983. Structural determination of the capsular polysaccharide antigen of type II Group B *Streptococcus*. J. Biol. Chem. 258:1793-1798.

23. Jennings, H. J. and R. K. Sood. 1994. Synthetic glycoconjugates as human vaccines. p. 325-371. In: Y. C. Lee and R. T. Lee, Neoglycoconjugates: Preparation and applications. Academic Press, New York.

24. Kang, D., Liu, G., Lundstrom, A. et al. 1998 A peptidoglycan recognition protein in innate immunity conserved from insects to humans. Proc. Natl. Acad. Sci. USA. 95:10078-10082.

25. Kasper, D. L., C. J. Baker, R. S. Baltimore, J. H. Crabb, G. Schiffman and H. J. Jennings. 1979. Immunodeterminant specificity of human immunity to type III group B *Streptococcus*. J. Exp. Med. 149:327-339.

26. Knobloch, J. E. and P. N. Shaklee. 1997. Absolute molecular weight of low-molecular-weight heparins by size-exclusion chromatography with multiangle laser light scattering detection. Anal. Biochem. 245:231-241.

27. Lancefield, R. C. 1933. A serological differentiation of human and other groups of haemolytic streptococci. J. Exp. Med. 57:571-595.

28. Lancefield, R. C. 1938. A micro-precipitin technique for classifying hemolytic streptococci and improved methods for producing antigen. Proc. Soc. Exp. Biol. and Med. 38:473-478.

29. Lancefield, R. C., M. McCarty and W. N. Everly. 1975. Multiple mouse-protective antibodies directed against group B streptococci: Special reference to antibodies effective against protein antigens. J. Exp. Med. 142:165-179.

30. Madoff, L. C., L. C. Paoletti, J. Y. Tai and D. L. Kasper. 1994. Maternal immunization of mice with Group B streptococcal type III polysaccharide-beta C protein conjugate elicits protective antibody to multiple serotypes. J. Clin. Invest. 94:286-292.

31. Marques, M. B., D. L. Kasper, A. Shroff, F. Michon, H. J. Jennings and M. R. Wessels. 1994. Functional activity of antibodies to the group B polysaccharide of group B streptococci elicited by a polysaccharide-protein conjugate vaccine. Infect. Immun. 62:1593-1599.

32. Mäkelä, P. R. H., H. Peltola, H. Kayhty, et al. 1977. Polysaccharide vaccines of group A *Neisseria meningitidis* and *Haemophilus influenzae* type b: A field trial in Finland. J. Infect. Dis. 136:543-50.

33. Michon, F., J. R. Brisson, A. Dell, D. L. Kasper and H. J. Jennings. 1988. Multiantennary group-specific polysaccharide of group B *Streptococcus*. Biochem. 27:5341-5351.

34. Peltola, A., H. Käyhty, A. Sivonen and P. R. H. Mäkelä. 1977. *Haemophilus influenzae* type b capsular polysaccharide vaccine in children: A double blind field study of 100,000 vaccines 3 months to 5 years of age in Finland. Pediatrics 60:730-737.

35. Peltola, H., P. R. H. Mäkelä, H. Jousimies, et al. 1977. Clinical efficacy of meningococcal group A vaccine in children three months to five years of age. N. Engl. J. Med. 297:686-691.

36. Reuter, G. and R. Schauer. 1994. Determination of sialic acids. p. 168-199. In: W. J. Lennarz and G. W. Hart, Methods in Enzymology Vol. 230 Techniques in Glycobiology. Academic Press, New York.

37. Robbins, J. B. and R. Schneerson. 1990. Polysaccharide-protein conjugates: A new generation of vaccines. J. Infect. Dis. 161:821-832.

38. Scwander, R., Dziarski R., Wesche, H. et al. 1999. Peptidoglycan- and lipoteichoic acid-induced cell activation is mediated by toll-like receptor 2. J. Biol. Chem. 274:17406-17409.

39. Smith, A. L. and J. Haas. 1991. Neonatal Bacterial Meningitis. p. 313-333. In: W. M. Scheld, R. J. Whitley and D. T. Durack, Infections of the Central Nervous System. Raven Press, Ltd., New York, 40. Tsunashima, T., K: Moro, B. Chu and T.-Y. Liu. 1978. Characterization of group C meningococcal polysaccharide by light-scattering spectroscopy. III. Determination of molecular weight, radius of gyration, and translational diffusional coefficient. Biopolymers 17:251-265.

41. von Hunolstein, C., L. Nicolini, S. D'Ascenzi, C. Volpe, G. Alfarone and G. Orefici. 1993. Sialic acid and biomass production by *Streptococcus agalactiae* under different growth conditions. Appl. Microbiol. Biotechnol. 38:458-462.

42. Wessels, M. R., W. J. Benedi, H. J. Jennings, F. Michon, J. L. DiFabio and D. L. Kasper. 1989. Isolation and characterization of type IV group B *Streptococcus* capsular polysaccharide. Infect. Immun. 57:1089-1094.

43. Wessels, M. R., J. L. DiFabio, V. J. Benedi, et al. 1991. Structural determination and immunochemical characterization of the type V group B *Streptococcus* capsular polysaccharide. J. Biol. Chem. 266:6714-6719.

44. Wessels, M. R., L. C. Paoletti, D. L. Kasper, et al. 1990. Immunogenicity in animals of a polysaccharide-protein conjugate vaccine against type III group B *Streptococcus*. J. Clin. Invest. 86:1428.1433.

45. Wessels, M. R., L. C. Paoletti, A. K. Rodewald, et al. 1993. Stimulation of protective antibodies against type 1*a* and 1*b* group B streptococci by a type Ia polysaccharide-tetanus toxoid conjugate vaccine. Infect. Immun. 61:4760-4766.

46. Wessels, M. R., V. Pozsgay, D. L. Kasper and H. J. Jennings. 1987. Structure and immunochemistry of an oligopolysaccharide repeating unit of the capsule polysaccharide of Type III Group B *Streptococcus*: A revised structure for the Type III Group B streptococcal polysaccharide antigen. J. Biol. Chem. 262:8262-8267.
47. Wyle, S. A., M. S. Artenstein, B. L. Brandt, et al. 1972. Immunologic response of man to group B meningococcal polysaccharide vaccines. J. Infect. Dis. 126:514-522.
48. Yang, R. B., Mark, M. R., Gray, A., et al. 1998. Toll-like receptor 2 mediates lipopolysaccharide-induced cellular signaling. Nature. 395:284-288.
49. Tipson, R. S. and Horton, D., *Advances in Carbohydrate Chemistry and Biochemistry*, Vol. 41, 1983, Academic Press, NY.
50. Westphal et al., *Methods in Carbohydrate Chemistry*, vol. V, 1965, Academic Press, NY.
51. Theodora W. Greene and Peter G. M. Wuts, *Protective Groups in Organic Syntheses,* 2nd Ed. (1991).
52. Kohler and Milstein (1975) *Nature* 256:495-497.
53. Takeda et al. (1985) *Nature* 314:452.
54. Campbell (1985) *Laboratory Techniques in Biochemistry and Molecular Biology*, Vol. 13, Burdon, et al. (eds.), Elsevier Science Publishers, Amsterdam.
55. Schneerson, R., et al. (1980) *J. Exp. Med.* 1952:361-476.
56. Marburg, S., et al. (1986) *J. Am. Chem. Soc.* 108:5282-5287.
57. Grossman, M. and Cohen, S. N., in "*Basic and Clinical Immunology*", 7th Ed., (Stites, D. P. and Terr, A. T. eds., Appleton & Lange 1991) Chapter 58 "Immunization".
58. Paoletti, et al. (1997) *J. Infectious Diseases,* 175:1237-9.
59. L. Warren, (1959) 1 *Biol. Chem.* 234, 1971.

What is claimed is:

1. A method of purifying a polysaccharide from a stock, wherein the stock comprises the polysaccharide and cellular components, the method comprising:
    contacting the stock with a first reagent to form a first mixture, wherein the first reagent is a base and wherein the pH of the first mixture is in the range of 9-15;
    separating the polysaccharide from at least some of the cellular components to form a separated composition comprising the polysaccharide and a residual amount of the cellular components;
    contacting the separated composition with a second reagent to form a second mixture, the second reagent being a base and wherein the pH of the second mixture is in the range of 9-15 and contacting is carried out at 40° C.-100° C.; and
    purifying the polysaccharide from at least some of the residual amount of the cellular components to form a purified composition:,
    wherein the polysaccharide is derived from *Neisseria meningitidis* type Y; and
    wherein the second contacting step and the purifying step do not comprise column chromatography.

2. The method according to claim 1, wherein the polysaccharide contains N-acetyl groups and wherein at least a portion of these N-acetyl groups are hydrolyzed by treatment with the second reagent.

3. The method according to claim 2, wherein a percentage of N-acetyl groups present on the polysaccharide that are hydrolyzed are then re-acylated sufficiently to maintain immunogenic properties of native polysaccharides.

4. The method according to claim 3, further comprising the steps of contacting the purified polysaccharide with an acylating reagent and purifying the acylated polysaccharide.

5. The method according to claim 4, wherein the acylating agent is acetic anhydride, acetyl chloride, pentafluorophenyl acetate or 4-nitrophenyl acetate.

6. The method according to claim 1, wherein at least One of the first reagent and the second reagent comprises an organic base.

7. The method according to claim 1, wherein at least one of the first reagent and the second reagent comprises an inorganic base.

8. The method according to claim 7, wherein the inorganic base comprises NaOH, KOH or LiOH.

9. The method according to any of claims 1, wherein the first reagent comprises a reducing agent.

10. The method according to claim 9, wherein the reducing reagent is chosen from NaBH4, NaCNBH3, lithium tri-sec-butylborohydride, NaBH(OCOCH3)3, lithium aluminum hydride, dithiothreitol, and p-mercaptoethanol.

11. The method according to claim 1, wherein the pH of the first mixture is from about 9 through about 13.

12. The method according to claim 1, wherein the pH of the second mixture is from about 11 through about 14.

13. The method according to claim 1, wherein the first reagent comprises about 1 N NaOH and NaBH4, and the second reagent comprises about 2 N NaOH.

14. The method according to claim 1, wherein the cellular components comprise protein and nucleic acid, wherein the cellular components are microbial in origin, wherein the first mixture hydrolyzes one or more bonds that provide for the direct or indirect attachment of the polysaccharide with the cellular components, and wherein the second mixture degrades proteins and nucleic acids.

15. The method according to claim 1, wherein separating the polysaccharide is by chromatography.

16. The method according to claim 1, wherein separating the polysaccharide is by membrane-filtration.

17. The method according to claim 1, wherein purifying the polysaccharide is by membrane-filtration.

18. The method according to claim 1, wherein the polysaccharide is a lipopolysaccharide.

19. The method according to claim 1, wherein the polysaccharide is a capsular polysaccharide, sub-capsular polysaccharide, or exopolysaccharide.

20. The method according to claim 1, wherein the polysaccharide is a capsular polysaccharide.

21. The method according to claim 3, further comprising the steps of contacting the purified polysaccharide with an acylating reagent and purifying the acylated polysaccharide; wherein
    the first reagent further comprises a reducing agent,
    the base is chosen from NaOH, KOH, and LiOH;
    the second reagent comprises a base chosen from NaOH, KOH, and LOH;
    separating the polysaccharide is by membrane-filtration that includes the use of tangential flow filtration with an ultrafiltration membrane;
    purifying the polysaccharide is by membrane-filtration that includes the use of tangential flow filtration with an ultrafiltration membrane; and
    the acylating reagent is acetic anhydride.

22. The method according to claim 21, wherein the purified polysaccharide contains less than about 5% by mass of nucleic acid and less than about 5% by mass protein.

23. The method according to claim 22, wherein the purified polysaccharide contains less than about 1% by mass of nucleic acid and less than about 1% by mass protein, and wherein the purity of the purified polysaccharide is 80%-100%.

24. The method according to claim 23, wherein the purity of the purified polysaccharide is 90%-100%.

25. The method according to claim 24, wherein the maximum temperature during which the separated composition is contacted with the second reagent is 30° C.-90° C. hotter than the maximum temperature during which the stock is contacted with the first reagent.

26. A method of purifying a polysaccharide from a stock, wherein the stock comprises the polysaccharide and cellular components, the method comprising:
contacting the stock with a first reagent to form a first mixture, wherein the first reagent comprises a base and a reducing agent and wherein the pH of the first mixture is in the range of 9-15;
separating the polysaccharide from at least some of the cellular components to form a separated composition comprising the polysaccharide and a residual amount of the cellular components; and recovering the purified polysaccharide.

27. The method of claim 26, further comprising the following steps before recovering the purified polysaccharide:
contacting the separated composition with a second reagent to form a second mixture, the second reagent being a base and wherein the pH of the second mixture is in the range of 9-15; and
purifying the polysaccharide from at least some of the residual amount of the cellular components to form a purified composition.

28. The method of any of claims 26-27, wherein the reducing reagent is chosen from NaBH4, NaCNBH3, lithium tri-sec-butylborohydride, NaBH(OCOCH3)3, lithium aluminum hydride, dithiothreitol, and p-mercaptoethanol.

29. The method of any of claims 26-27, wherein separating the polysaccharide is by membrane-filtration.

30. The method of claim 29, wherein the membrane-filtration includes the use of tangential flow filtration with an ultrafiltration membrane.

* * * * *